US012559759B2

(12) United States Patent
Chan et al.

(10) Patent No.: US 12,559,759 B2
(45) Date of Patent: Feb. 24, 2026

(54) FUSION POLYPEPTIDES

(71) Applicant: DANISCO US INC, Palo Alto, CA (US)

(72) Inventors: Jimmy Chan, Palo Alto, CA (US); David A. Estell, Palo Alto, CA (US); Amy Deming Liu, Palo Alto, CA (US); Michael C. Miller, Palo Alto, CA (US); Igor Nikolaev, Leiden (NL)

(73) Assignee: Danisco US Inc., Palo Alto, CA (US)

( * ) Notice: Subject to any disclaimer, the term of this patent is extended or adjusted under 35 U.S.C. 154(b) by 1092 days.

(21) Appl. No.: 17/437,189

(22) PCT Filed: Mar. 9, 2020

(86) PCT No.: PCT/US2020/021685
§ 371 (c)(1),
(2) Date: Sep. 8, 2021

(87) PCT Pub. No.: WO2020/185669
PCT Pub. Date: Sep. 17, 2020

(65) Prior Publication Data
US 2023/0159937 A1 May 25, 2023

Related U.S. Application Data

(60) Provisional application No. 62/815,912, filed on Mar. 8, 2019.

(51) Int. Cl.
*C12N 15/62* (2006.01)
*C12N 9/60* (2006.01)

(52) U.S. Cl.
CPC .......... *C12N 15/62* (2013.01); *C07K 2319/50* (2013.01); *C12N 9/60* (2013.01)

(58) Field of Classification Search
CPC .............. C07K 16/32; C07K 2317/14; C07K 2319/00; C07K 2319/50; C12N 9/60; C12N 15/62; C12Y 304/21061
USPC ....................................................... 435/69.7
See application file for complete search history.

(56) References Cited

U.S. PATENT DOCUMENTS

| | | | |
|---|---|---|---|
| 4,816,567 | A | 3/1989 | Cabilly et al. |
| 8,198,046 | B2 | 6/2012 | Wang et al. |
| 2014/0024067 | A1 | 1/2014 | Wang et al. |

FOREIGN PATENT DOCUMENTS

| | | | |
|---|---|---|---|
| EP | 0215594 A2 | 3/1987 |
| EP | 0137280 B1 | 3/1992 |
| JP | 2009-542258 A | 12/2009 |
| WO | 9600787 | 1/1996 |

OTHER PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*
Alexopoulos, C. J. (1962), Introductory Mycology, Wiley, New York—Book not included.
Ausubel, Frederick M. et al., Short Protocols in Molecular Biology, 3rd ed., Wiley & Sons, 1995—Book not included.
Barclay, Stephen L. et al., Efficient Transformation of Dictyostelium discoideum Amoebae, Molecular and Cellular Biology, Dec. 1983, pp. 2117-2130, vol. 3, No. 12.
Boel, E. et al., Two different types of intervening sequences in the glucoamylase gene from Aspergillus niger, The EMBO Journal, 1984, pp. 1581-1585, vol. 3, No. 7.
Contreras, Roland et al., Efficient KEX2-Like Processing of a Glucoamyiase-Interleukin-6 Fusion Protein by Aspergillus Nidulans and Secretion of Mature Interleukin-6, Bio/Technology, Apr. 1991, pp. 378-381, vol. 9.
Fuller Robert S. et al., Yeast prohormone processing enzyme (KEX2 gene product) is a Ca2'-dependent serine protease, Proc. Natl. Acad. Sci. USA, Mar. 1989, pp. 1434-1438, vol. 86.
Gines, Maria Jesus et al., Aspergillus oryzae has two nearly identical Taka-amylase genes, each containing eight introns, Gene, 1989, pp. 107-117, vol. 79.
Gwynne, David I. et al., Genetically Engineered Secretion of Active Human Interferon and a Bacterial Endoglucanase From Aspergillus Nidulans, Bio/Technology, Jul. 1987, pp. 713-719, vol. 5.
Hynes, Michael J. et al., Isolation of Genomic Clones Containing the amdS Gene of Aspergillus nidulans and Their Use in the Analysis of Structural and Regulatory Mutations, Molecular and Cellular Biology, Aug. 1983, pp. 1430-1439, vol. 3, No. 8.
Kelly, Joan M. et al., Transformation of Aspergillus niger by the amdS gene of Aspergillus nidulans, The EMBO Journal, 1985, pp. 475-479, vol. 4, No. 2.
Korman, David R. et al., Cloning, characterization, and expression of two α-amylase genes from Aspergillus niger var. awamori, Current Genetics, 1990, pp. 203-212, vol. 17.
Libby, Carol Baker et al., Effect of amino acid deletions in the O-glycosylated region of Aspergillus awamori glucoamylase, Protein Engineering, 1994, pp. 1109-1114, vol. 7, No. 9.
Lockington, Robin A. et al., Cloning and characterization of the ethanol utilization regulon in Aspergillus nidulans, Gene, 1985, pp. 137-149, vol. 33.
Mcknight, Gary L. et al., Nucleotide Sequence of the Triosephosphate Isomerase Gene from Aspergillus nidulans: Implications for a Differential Loss of Introns, Cell, Jul. 4, 1986, pp. 143-147, vol. 46.
Mullaney Edward J. et al., Primary structure of the trpC gene from Aspergillus nidulans, Mol Gen Genet, 1985, pp. 37-45, vol. 199.
Nunberg, Jack H. et al., Molecular Cloning and Characterization of the Glucoamylase Gene of Aspergillus awamori, Molecular and Cellular Biology, Nov. 1984, pp. 2306-2315, vol. 4, No. 11.
(Continued)

*Primary Examiner* — Tekchand Saidha
*Assistant Examiner* — Mohammad Y Meah

(57) ABSTRACT

Provided herein, inter alia, are fusion DNA constructs comprising improved protease recognition sequences for expressing and purifying one or more polypeptides of interest as well as methods for producing one or more polypeptides of interest in a recombinant host cell.

7 Claims, 17 Drawing Sheets

Specification includes a Sequence Listing.

(56)    References Cited

OTHER PUBLICATIONS

Paloheimo, Marja et al., High-Yield Production of a Bacterial Xylanase in the Filamentous Fungus *Trichoderma reesei* Requires a Carrier Polypeptide with an Intact Domain Structure, Applied and Environmental Microbiology, Dec. 2003, pp. 7073-7082, vol. 69, No. 12.

Pennell, C.A. et al., In vitro production of recombinant antibody fragments in Pichia pastoris, Research in Immunology, Jul. 10, 1998, pp. 599-603.

Pentilla, Merja et al., A versatile transformation system for the cellulolytic filamentous fungus *Trichoderma reesei*, Gene, 1987, pp. 155-164, vol. 61.

Verma R. et al., Antibody engineering: Comparison of bacterial, yeast, insect and mammalian expression systems, Journal of Immunological Methods, 1998, pp. 165-181, vol. 216.

Ward, Michael et al., Improved Production of Chymosin in Aspergillus by Expression as a Glucoamylase-Chymosin Fusion, Bio/Technology, May 1990, pp. 435-440, vol. 8.

Yelton, Melanie M. et al., Transformation of Aspergillus nidulans by using a trpC plasmid, Proc. Natl. Acad. Sci. USA, Mar. 1984, pp. 1470-1474, vol. 81.

International Search Report and Written Opinion, PCT/US2020/021685, mailed Sep. 17, 2020.

* cited by examiner $X_8 X_7 X_6 X_5 X_4 X_3 X_2 X_1 - K R - X_{-1} X_{-2} X-$

| Signal | Carrier Protein | Linker | Protein of Interest | caggtcaccctctccggagagcggccctgctctcgtcaagcccacgcagacccctcacgctgcttcagcgcttcagc
accaggcggcatgagcgtcggctggatccgccagcctcctgctgcaggccctcgagtggctcgccgacatctgtgtggggacgacaagaagg
actacaacccagctcaagcctcaccatcagcaagatccgcgctcaccaactgtcctgaagtcaccacacatggaccc
cgccgacaccgccaactactgcgccgcagcatgatcaccaactggtacttcgactggggcggcagcaccgtcaccgtcag
cagcgcctccacgaaggcccagcgtcttccgctcgctccagcagcaagagcaccctccggcgggcacgctgcctcggctgctggt
caaggactacttcccgagcgtgtcacgcagctcagctggaactctggcgtcccgacgcccctgacacacgctccaccagccagcc
cagcggcctctactccctgagcagcgtgtcacgcgtgtctgcccctcggcgtcccagctcctcctgctcctgctcgaggctgcttg
tagcaacaccaaggtcgacaccgctgccgagcccaagagctggtcgacaagacccacctgccctcgtgccctgctgcgtcgtgacgtc
gcggccctcggtctcttcgtcctccgagctcaggacgacctcatgatctcgcgacggcgtcgaggtccacaacgctaagacgaacccgcgaggagcagt
agccacgaggaccctgaggtcaagtttaactggtatgtcgacggcgtcgaggtccacaacgctaagacgaagagtacaagtgcaaggtcagcaac
acaacagcacctaccgcgtgctctatcgagaagaccatctccaaggtcaaggccagcgtctccctgcgcgagcgccagcgcagccgg
aaggccctgcctgctcctatcgagaagaccatctccaaggcaaaggccagcgtctccctgcgcgagcgccagcgcagccgcg
agaggagatgacgaagaaccaggtgagctgacctgacacacgacccgctcgtcaaggtctctcctgtacagcaagctcaccgtcgacaag
ggccagctgagaacaactacaagacccccgagctcctgtcctcgctccgactccgacgctcgtctttcctgtacagcaagctcaccgtcgacaag
tcccgctggcagcagggcaacgtcttcagctgctgcgtcgtcatgcacgaggccctccacaaccactacacaccagagtccctcgctcagc
cccggcaagtaa

*FIG. 5A* qvtlresgpalvkptqtltctfsgfslstsgmsvgwirqppgkalewladiwwddkkdynpslksrltiskdtsknqvvikvtnmdpa
dtatyycarsmitnwyfdwgagttvtvssastkgpsvfplapssksgtaalgclvkdyfpepvtvswnsgaltsgvhtfpavlqss
glyslssvvtvpsslgtqtyicnvnhkpsntkvdtrvepkscdkthtcppcpapellggpsvflfppkpkdtlmisrtpevtcvvvdvsh
edpevkfnwyvdgvevhnaktkpreeqynstyrvvsvltvlhqdwlngkeykckvsnkalpapiektiskakgqprepqvytlppsr
eemtknqvsltclvkgfypsdiavewesngqpennykttppvldsdgsfflysklitvdksrwqqgnvfscsvmhealnhhytqkslsl
spgk

*FIG. 5B*

Herceptin HC amino acid sequence

EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDTRVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK

FIG. 10A

Herceptin HC DNA sequence in pJC159

```
GAGGTGCAGCTGGTCGAGTCCGGCGGCGGACTGGTGCAGCCCGGAGGCTCCCTGCG
TCTGAGCTGTGCCGCTTCTGGCTTCAACATCAAGGACACCTATATCCACTGGGTCCG
GCAGGCCCCCGGCAAGGGCTTGGAGTGGGTCGCCCGCATCTACCCCACCAACGGAT
ATACGCGTTATGCCGATAGCGTTAAGGGCCGCTTTACGATCTCGGCGGATACCAGCA
AGAACACGGCTTATCTGCAGATGAACTCCCTTCGGGCCGAGGATACGGCCGTGTACT
ACTGTAGCCGTTGGGGAGGCGATGGATTCTACGCGATGGATTACTGGGGACAAGGT
ACCCTGGTCACAGTGTCCTCCGCCAGCACCAAGGGCCCTAGCGTCTTCCCCCTCGCC
CCAAGCAGCAAGTCGACCTCCGGCGGCACGGCGGCTTTGGGCTGCCTCGTCAAGGA
CTATTTCCCTGAACCAGTGACGGTCAGCTGGAACTCTGGTGCGCTCACTTCGGGCGT
CCACACTTTCCCCGCCGTCCTGCAGTCGTCGGGTCTGTACTCGCTGTCGAGCGTTGTC
ACAGTCCCAAGCAGCTCGCTCGGTACTCAGACTTATATCTGCAACGTCAACCACAAG
CCCTCTAACACCAAGGTCGACACTAGGGTGGAGCCGAAGTCCTGCGATAAGACACA
CACATGTCCACCCTGCCCGGCCCCCGAGCTGCTGGGCGGCCCCTCCGTCTTTCTCTTT
CCGCCCAAGCCTAAGGACACGTTGATGATTTCGCGAACGCCGGAGGTGACCTGTGT
CGTCGTCGACGTTTCCCATGAGGATCCTGAGGTCAAGTTTAACTGGTACGTCGACGG
CGTCGAGGTCCATAACGCCAAGACCAAGCCCCGGGAGGAACAGTACAATAGCACTT
ACCGCGTGGTTTCTGTCCTCACCGTGCTGCACCAAGATTGGCTTAACGGAAAGGAAT
ACAAGTGCAAGGTGTCCAACAAGGCACTGCCCGCCCCCATCGAGAAGACTATCAGC
AAGGCGAAGGGCCAGCCTCGGGAACCCCAAGTGTATACCCTTCCGCCGTCCCGGGA
GGAGATGACCAAGAATCAGGTCTCCCTGACGTGCCTGGTTAAGGGCTTCTACCCCTC
TGACATCGCCGTCGAGTGGGAGAGCAATGGCCAGCCCGAGAACAACTACAAGACCA
CGCCCCCGGTCCTCGACAGCGACGGCAGCTTCTTCCTGTACTCCAAGCTGACGGTGG
ACAAGAGCCGTTGGCAACAGGGAAATGTTTTTTCGTGCTCGGTCATGCACGAGGCGT
TGCACAACCACTACACGCAGAAGTCCCTCTCGCTCTCTCCCGGAAAG
```

*FIG. 10B*

Herceptin HC DNA sequence in pJC158

GAGGTCCAGCTTGTCGAGAGCGGCGGCGGCCTCGTCCAACCTGGCGGATCCCTGCG
GCTCAGCTGCGCGGCTAGCGGCTTCAACATCAAGGATACGTACATTCACTGGGTGCG
CCAGGCCCCTGGAAAGGGCCTCGAGTGGGTCGCTCGGATCTACCCCACGAACGGCT
ACACCCGCTACGCTGACAGCGTCAAGGGCCGCTTCACCATTTCTGCCGACACGTCTA
AGAACACTGCATACCTCCAGATGAACTCCTTGCGCGCCGAGGACACCGCAGTCTACT
ACTGCTCCCGTTGGGGCGGCGACGGCTTTTACGCGATGGACTACTGGGGTCAGGGCA
CACTCGTGACAGTCAGCTCCGCCTCTACCAAGGGCCCTAGCGTGTTCCCCCTTGCCC
CCTCCTCTAAGTCGACCAGCGGCGGCACAGCCGCCCTCGGCTGCCTCGTCAAGGACT
ATTTCCCCGAACCGGTCACGGTCAGCTGGAACTCCGGCGCGCTCACTTCCGGCGTGC
ATACCTTTCCTGCCGTCCTGCAGTCTTCCGGCCTTTACTCCTTGTCCTCCGTCGTCACT
GTCCCCTCGTCCTCCCTTGGCACGCAGACGTACATTTGCAACGTCAACCACAAGCCT
TCGAACACAAAGGTCGACACCCGCGTTGAGCCCAAGTCTTGCGACAAGACCCATAC
CTGCCCTCCTTGCCCAGCACCCGAACTGCTTGGCGGACCCAGCGTCTTTCTGTTTCCG
CCAAAGCCAAAGGACACCCTTATGATTTCCCGAACCCCTGAAGTCACGTGCGTCGTT
GTCGATGTGAGCCACGAAGATCCCGAAGTCAAGTTTAACTGGTATGTCGACGGCGTC
GAGGTCCACAACGCCAAGACGAAGCCCCGCGAGGAGCAGTACAACTCCACGTACCG
CGTGGTCTCTGTCCTCACGGTCCTGCATCAGGACTGGCTCAACGGCAAGGAATACAA
GTGTAAGGTCAGCAACAAGGCTCTGCCGGCCCCTATTGAGAAGACCATCTCCAAGG
CCAAGGGCCAGCCCCGCGAACCACAAGTGTACACCCTGCCTCCCTCGCGAGAAGAG
ATGACAAAGAACCAGGTCAGCTTGACCTGCCTTGTTAAGGGTTTTTACCCATCGGAC
ATCGCAGTCGAGTGGGAGAGCAATGGCCAGCCAGAGAACAACTACAAGACCACGC
CCCCTGTCCTCGACAGCGACGGAAGCTTTTTCCTGTACTCTAAGCTTACAGTTGACA
AGAGCAGGTGGCAGCAGGGCAACGTCTTCAGCTGTAGCGTGATGCACGAAGCTCTG
CACAACCACTACACCCAGAAGTCTCTTAGCTTGAGCCCGGGAAAG

FIG. 10C

Herceptin LC amino acid sequence

DIQMTQSPSSLSASVGDRVTITCRASQDVNTAVAWYQQKPGKAPKLLIYSASFLYSGVP
SRFSGSRSGTDFTLTISSLQPEDFATYYCQQHYTTPPTFGQGTKVEITRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC

FIG. 11A

Herceptin LC DNA sequence

GACATCCAGATGACCCAGAGCCCCAGCAGCCTCAGCGCCTCTGTCGGCGACCGCGT
CACCATCACCTGCCGCGCCAGCCAGGACGTCAACACCGCCGTCGCCTGGTATCAGC
AGAAGCCCGGCAAGGCCCCCAAGCTCCTCATCTACAGCGCCAGCTTCCTCTACAGCG
GCGTCCCCAGCCGCTTCAGCGGCAGCCGCAGCGGCACCGACTTCACCCTCACCATCA
GCAGCCTCCAGCCCGAGGACTTCGCCACCTACTACTGCCAGCAGCACTACACCACCC
CCCCCACCTTCGGCCAGGGCACCAAGGTCGAGATCACCCGCACCGTCGCGGCGCCA
AGCGTCTTTATCTTCCCCCCCAGCGACGAGCAGCTCAAGAGCGGCACCGCCAGCGTC
GTCTGCCTCCTCAACAACTTCTACCCCCGCGAGGCCAAGGTCCAGTGGAAGGTCGAC
AACGCCCTCCAGAGCGGCAACAGCCAGGAGAGCGTCACCGAGCAGGACAGCAAGG
ACTCCACCTACAGCCTCAGCAGCACCCTCACCCTCTCCAAGGCCGACTACGAGAAGC
ACAAGGTCTACGCCTGCGAGGTCACCCACCAGGGCCTCAGCTCCCCCGTCACCAAG
AGCTTCAACCGCGGCGAGTGC

FIG. 11B

CBH1 core amino acid sequence

MYRKLAVISAFLATARAQSACTLQSETHPPLTWQKCSSGGTCTQQTGSVVIDANWRWT
HATNSSTNCYDGNTWSSTLCPDNETCAKNCCLDGAAYASTYGVTTSGNSLSIGFVTQSA
QKNVGARLYLMASDTTYQEFTLLGNEFSFDVDVSQLPCGLNGALYFVSMDADGGVSK
YPTNTAGAKYGTGYCDSQCPRDLKFINGQANVEGWEPSSNNANTGIGGHGSCCSEMDI
WEANSISEALTPHPCTTVGQEICEGDGCGGTYSDNRYGGTCDPDGCDWNPYRLGNTSF
YGPGSSFTLDTTKKLTVVTQFETSGAINRYYVQNGVTFQQPNAELGSYSGNELNDDYCT
AEEAEFGGSSFSDKGGLTQFKKATSGGMVLVMSLWDDYYANMLWLDSTYPTNETSST
PGAVRGSCSTSSGVPAQVESQSPNAKVTFSNIKFGPIGSTGNPSGGNPPGGNPPGTTTTRR
PATTTGSSPGP

FIG. 12A

CBH1 core DNA sequence

ATGTATCGGAAGTTGGCCGTCATCTCGGCCTTCTTGGCCACAGCTCGTGCTCAGTCG
GCCTGCACTCTCCAATCGGAGACTCACCCGCCTCTGACATGGCAGAAATGCTCGTCT
GGTGGCACGTGCACTCAACAGACAGGCTCCGTGGTCATCGACGCCAACTGGCGCTG
GACTCACGCTACGAACAGCAGCACGAACTGCTACGATGGCAACACTTGGAGCTCGA
CCCTATGTCCTGACAACGAGACCTGCGCGAAGAACTGCTGTCTGGACGGTGCCGCCT
ACGCGTCCACGTACGGAGTTACCACGAGCGGTAACAGCCTCTCCATTGGCTTTGTCA
CCCAGTCTGCGCAGAAGAACGTTGGCGCTCGCCTTTACCTTATGGCGAGCGACACGA
CCTACCAGGAATTCACCCTGCTTGGCAACGAGTTCTCTTTCGATGTTGATGTTTCGCA
GCTGCCGTAAGTGACTTACCATGAACCCCTGACGCTATCTTCTTGTTGGCTCCCAGCT
GACTGGCCAATTCAAGGTGCGGCTTGAACGGAGCTCTCTACTTCGTGTCCATGGACG
CGGATGGTGGCGTGAGCAAGTATCCCACCAACACCGCTGGCGCCAAGTACGGCACG
GGGTACTGTGACAGCCAGTGTCCCCGCGATCTGAAGTTCATCAATGGCCAGGCCAA
CGTTGAGGGCTGGGAGCCGTCATCCAACAACGCGAACACGGGCATTGGAGGACACG
GAAGCTGCTGCTCTGAGATGGATATCTGGGAGGCCAACTCCATCTCCGAGGCTCTTA
CCCCCCACCCTTGCACGACTGTCGGCCAGGAGATCTGCGAGGGTGATGGGTGCGGC
GGAACTTACTCCGATAACAGATATGGCGGCACTTGCGATCCCGATGGCTGCGACTGG
AACCCATACCGCCTGGGCAACACCAGCTTCTACGGCCCTGGCTCAAGCTTTACCCTC
GATACCACCAAGAAATTGACCGTTGTCACCCAGTTCGAGACGTCGGGTGCCATCAA
CCGATACTATGTCCAGAATGGCGTCACTTTCCAGCAGCCCAACGCCGAGCTTGGTAG
TTACTCTGGCAACGAGCTCAACGATGATTACTGCACAGCTGAGGAGGCAGAATTCG
GCGGATCCTCTTTCTCAGACAAGGGCGGCCTGACTCAGTTCAAGAAGGCTACCTCTG
GCGGCATGGTTCTGGTCATGAGTCTGTGGGATGATGTGAGTTTGATGGACAAACATG
CGCGTTGACAAAGAGTCAAGCAGCTGACTGAGATGTTACAGTACTACGCCAACATG
CTGTGGCTGGACTCCACCTACCCGACAAACGAGACCTCCTCCACACCCGGTGCCGTG
CGCGGAAGCTGCTCCACCAGCTCCGGTGTCCCTGCTCAGGTCGAATCTCAGTCTCCC
AACGCCAAGGTCACCTTCTCCAACATCAAGTTCGGACCCATTGGCAGCACCGGCAA
CCCTAGCGGCGGCAACCCTCCCGGCGGAAACCCGCCTGGCACCACCACCACCCGCC
GCCCAGCCACTACCACTGGAAGCTCTCCCGGACCT

*FIG. 12B*

SEQUENCE LISTING

```
<160> NUMBER OF SEQ ID NOS: 94

<210> SEQ ID NO 1
<211> LENGTH: 10
<212> TYPE: PRT
<213> ORGANISM: Artificial Sequence
<220> FEATURE:
<223> OTHER INFORMATION: Sequence is synthesized.
<220> FEATURE:
<221> NAME/KEY: MISC_FEATURE
<222> LOCATION: (7)..(7)
<223> OTHER INFORMATION: basic amino acid
<220> FEATURE:
<221> NAME/KEY: MISC_FEATURE
<222> LOCATION: (8)..(8)
<223> OTHER INFORMATION: basic amino acid

<400> SEQUENCE: 1

Thr Ser Val Ala Val Glu Xaa Xaa Gln Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 2

Phe Ser Val Ala Val Glu Lys Arg Gln Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 3

Ala Ser Val Ala Val Glu Lys Arg Gln Val
1               5                   10

<210> SEQ ID NO 4
<211> LENGTH: 10
<212> TYPE: PRT
```

```
<213> ORGANISM: Artificial Sequence
<220> FEATURE:
<223> OTHER INFORMATION: Sequence is synthesized.

<400> SEQUENCE: 4

Met Ser Val Ala Val Glu Lys Arg Gln Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 5

Gln Ser Val Ala Val Glu Lys Arg Gln Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 6

Arg Ser Val Ala Val Glu Lys Arg Gln Val
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 7

Tyr Ser Val Ala Val Glu Lys Arg Gln Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 8

Thr Phe Val Ala Val Glu Lys Arg Gln Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 9

Thr His Val Ala Val Glu Lys Arg Gln Val
1               5                   10

<210> SEQ ID NO 10
<211> LENGTH: 10
<212> TYPE: PRT
<213> ORGANISM: Artificial Sequence
```

-continued

```
<220> FEATURE:
<223> OTHER INFORMATION: Sequence is synthesized.

<400> SEQUENCE: 10

Thr Lys Val Ala Val Glu Lys Arg Gln Val
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 11

Thr Leu Val Ala Val Glu Lys Arg Gln Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 12

Thr Met Val Ala Val Glu Lys Arg Gln Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 13

Thr Pro Val Ala Val Glu Lys Arg Gln Val
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 14

Thr Gln Val Ala Val Glu Lys Arg Gln Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 15

Thr Arg Val Ala Val Glu Lys Arg Gln Val
1               5                   10

<210> SEQ ID NO 16
<211> LENGTH: 10
<212> TYPE: PRT
<213> ORGANISM: Artificial Sequence
<220> FEATURE:
```

```
<223> OTHER INFORMATION: Sequence is synthesized.

<400> SEQUENCE: 16

Thr Val Val Ala Val Glu Lys Arg Gln Val
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 17

Thr Ser Val His Val Glu Lys Arg Gln Val
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 18

Thr Ser Val Lys Val Glu Lys Arg Gln Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 19

Thr Ser Val Arg Val Glu Lys Arg Gln Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 20

Thr Ser Val Ala Leu Glu Lys Arg Gln Val
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 21

Thr Ser Val Ala Val Phe Lys Arg Gln Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Sequence is synthesized.
```

```
<400> SEQUENCE: 22

Thr Ser Val Ala Val Trp Lys Arg Gln Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 23

Thr Ser Val Ala Val Glu Lys Arg Asp Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 24

Thr Ser Val Ala Val Glu Lys Arg Gly Val
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 25

Thr Ser Val Ala Val Glu Lys Arg Gln Phe
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 26

Thr Ser Val Ala Val Glu Lys Arg Gln Leu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 27

Thr Ser Val Ala Val Glu Lys Arg Gln Val Glu Leu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Sequence is synthesized.
```

```
<400> SEQUENCE: 28

Thr Ser Val Ala Val Glu Lys Arg Gln Val Thr Ile
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 29

Thr Ser Val Ala Val Glu Lys Arg Gln Val Thr Val
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 30

Thr His Val Ala Val Glu Lys Arg Gln Val Thr Ile
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 31

Thr His Val Ala Val Glu Lys Arg Asp Val Thr Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 32

Thr His Val Ala Val Glu Lys Arg Gln Val Ala Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 33

Glu His Val Ala Val Glu Lys Arg Gln Val Thr Leu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 34
```

```
Thr Asn Val Ala Val Glu Lys Arg Asp Val Thr Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 35

Thr Asn Val Ala Val Glu Lys Arg Gln Val Ala Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 36

Thr Ser Val Ala Leu Trp Lys Arg Gln Val Thr Leu
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 37

Thr Ser Val Met Leu Glu Lys Arg Gln Val Thr Leu
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 38

Thr Ser Val Ala Leu Glu Lys Arg Gln Ile Thr Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 39

Thr Ser Val Ala Leu Glu Lys Arg Gln Val Ala Leu
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 40
```

-continued

```
Thr His Val Ala Leu Glu Lys Arg Gln Val Thr Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 41

Thr Ser Val Ala Val Glu Lys Arg Asp Val Ala Leu
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 42

Thr His Val Met Leu Glu Lys Arg Gln Val Thr Leu
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 43

Thr Lys Val Met Leu Glu Lys Arg Gln Val Thr Leu
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 44

Thr His Val Ala Val Glu Lys Arg Asp Val Ala Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 45

Thr His Val Ala Leu Trp Lys Arg Gln Val Thr Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 46

Thr Lys Val Ala Val Glu Lys Arg Asp Leu Thr Leu
```

-continued

```
1               5                  10
```

```
<210> SEQ ID NO 47
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 47

Thr Asn Val Ala Val Glu Lys Arg Asp Leu Thr Leu
1               5                  10

<210> SEQ ID NO 48
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 48

Glu His Val Ala Val Trp Lys Arg Gln Val Thr Leu
1               5                  10

<210> SEQ ID NO 49
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 49

Glu His Val Ala Leu Glu Lys Arg Gln Val Thr Leu
1               5                  10

<210> SEQ ID NO 50
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 50

Glu Ser Val Ala Leu Trp Lys Arg Gln Val Thr Leu
1               5                  10

<210> SEQ ID NO 51
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 51

Glu Ser Val Ala Leu Trp Lys Arg Gln Val Thr Leu
1               5                  10

<210> SEQ ID NO 52
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 52

Thr Ser Val Ala Leu Glu Lys Arg Asp Val Ala Leu
1               5                  10
```

```
<210> SEQ ID NO 53
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 53

Thr His Val Ala Leu Glu Lys Arg Asp Val Ala Leu
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 54

Thr Lys Val Arg Val Glu Lys Arg Asp Leu Thr Leu
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 55

Thr Asn Val Ala Leu Glu Lys Arg Asp Val Ala Leu
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 56

Glu His Val Ala Leu Trp Lys Arg Gln Val Thr Leu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 57

Glu Pro Val Ala Leu Trp Lys Arg Gln Val Thr Leu
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 58

Asn His Val Ala Leu Trp Lys Arg Gln Val Thr Leu
1               5                   10
```

```
<210> SEQ ID NO 59
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 59

Arg Ser Val Arg Val Glu Lys Arg Asp Leu Thr Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 60

Arg Lys Val Arg Val Glu Lys Arg Asp Val Thr Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 61

Arg Lys Val Arg Val Glu Lys Arg Gln Leu Thr Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 62

Arg Lys Val Ala Val Glu Lys Arg Asp Leu Thr Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 63

Arg Lys Val Arg Val Glu Lys Arg Asp Leu Thr Leu
1               5                   10

<210> SEQ ID NO 64
<211> LENGTH: 6
<212> TYPE: PRT
<213> ORGANISM: Artificial Sequence
<220> FEATURE:
<223> OTHER INFORMATION: Sequence is synthesized.
<220> FEATURE:
<221> NAME/KEY: MISC_FEATURE
<222> LOCATION: (1)..(1)
<223> OTHER INFORMATION: basic amino acid
<220> FEATURE:
<221> NAME/KEY: MISC_FEATURE
<222> LOCATION: (2)..(2)
```

<223> OTHER INFORMATION: basic amino acid

<400> SEQUENCE: 64

Xaa Xaa Gln Val Thr Leu
1               5

<210> SEQ ID NO 65
<211> LENGTH: 10
<212> TYPE: PRT
<213> ORGANISM: Artificial Sequence
<220> FEATURE:
<223> OTHER INFORMATION: Sequence is synthesized.
<220> FEATURE:
<221> NAME/KEY: MISC_FEATURE
<222> LOCATION: (9)..(9)
<223> OTHER INFORMATION: basic amino acid
<220> FEATURE:
<221> NAME/KEY: MISC_FEATURE
<222> LOCATION: (10)..(10)
<223> OTHER INFORMATION: basic amino acid

<400> SEQUENCE: 65

Gly Pro Thr Ser Val Ala Val Glu Xaa Xaa
1               5                   10

<210> SEQ ID NO 66
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 66

Lys Ser Arg Ser
1

<210> SEQ ID NO 67
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 67

Ser Arg Ile Ser
1

<210> SEQ ID NO 68
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 68

Gly Gly Gly Ser
1

<210> SEQ ID NO 69
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 69

Thr Ser Thr Tyr
1

```
<210> SEQ ID NO 70
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 70

Ala Ser Ile Ser
1

<210> SEQ ID NO 71
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 71

Ala Thr Ala Ser
1

<210> SEQ ID NO 72
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 72

Thr Ala Ser Gln
1

<210> SEQ ID NO 73
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 73

Thr Ala Ser Leu
1

<210> SEQ ID NO 74
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 74

Ser Val Ile Ser
1

<210> SEQ ID NO 75
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 75

Asn Val Ile Ser
1
```

-continued

```
<210> SEQ ID NO 76
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 76

Thr Ser Arg Asp
1

<210> SEQ ID NO 77
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 77

Ser Pro Met Asp
1

<210> SEQ ID NO 78
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 78

Asp Leu Gly Glu
1

<210> SEQ ID NO 79
<211> LENGTH: 4
<212> TYPE: PRT
<213> ORGANISM: Artificial Sequence
<220> FEATURE:
<223> OTHER INFORMATION: Sequence is synthesized.

<400> SEQUENCE: 79

Thr Pro Thr Ala
1

<210> SEQ ID NO 80
<211> LENGTH: 10
<212> TYPE: PRT
<213> ORGANISM: Artificial Sequence
<220> FEATURE:
<223> OTHER INFORMATION: Sequence is synthesized.

<400> SEQUENCE: 80

Thr Ser Val Ala Val Glu Lys Arg Gln Val
1               5                   10

<210> SEQ ID NO 81
<211> LENGTH: 6
<212> TYPE: PRT
<213> ORGANISM: Artificial Sequence
<220> FEATURE:
<223> OTHER INFORMATION: Sequence is synthesized.

<400> SEQUENCE: 81

Thr Ser Val Ala Val Glu
1               5
```

```
<210> SEQ ID NO 82
<211> LENGTH: 450
<212> TYPE: PRT
<213> ORGANISM: Artificial Sequence
<220> FEATURE:
<223> OTHER INFORMATION: Sequence is synthesized.

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Thr Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
```

```
          370              375              380

Glu Ser Asn Gly Gln Pro Glu Asn Asn Tyr Lys Thr Thr Pro Pro Val
385             390              395              400

Leu Asp Ser Asp Gly Ser Phe Phe Leu Tyr Ser Lys Leu Thr Val Asp
                405              410              415

Lys Ser Arg Trp Gln Gln Gly Asn Val Phe Ser Cys Ser Val Met His
            420              425              430

Glu Ala Leu His Asn His Tyr Thr Gln Lys Ser Leu Ser Leu Ser Pro
        435              440              445

Gly Lys
    450
```

```
<210> SEQ ID NO 83
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 83

Tyr Leu Thr Ser Val Met Leu Glu Lys Arg Gln Val
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 84

Tyr Leu Thr His Val Met Leu Glu Lys Arg Gln Val
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 85

Tyr Pro Thr His Val Met Leu Glu Lys Arg Gln Val
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 86

Tyr Pro Thr His Val Ala Leu Glu Lys Arg Gln Val
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 87
```

```
Gly Leu Thr Ser Val Met Val Glu Lys Arg Gln Val
1               5                   10
```

```
<210> SEQ ID NO 88
<211> LENGTH: 12
<212> TYPE: PRT
<213> ORGANISM: Artificial Sequence
<220> FEATURE:
<223> OTHER INFORMATION: Sequence is synthesized.

<400> SEQUENCE: 88
```

```
Gly Leu Thr His Val Met Leu Glu Lys Arg Gln Val
1               5                   10
```

```
<210> SEQ ID NO 89
<211> LENGTH: 1350
<212> TYPE: DNA
<213> ORGANISM: Artificial Sequence
<220> FEATURE:
<223> OTHER INFORMATION: Sequence is synthesized.

<400> SEQUENCE: 89
```

```
gaggtgcagc tggtcgagtc cggcggcgga ctggtgcagc ccggaggctc cctgcgtctg      60
agctgtgccg cttctggctt caacatcaag gacacctata tccactgggt ccggcaggcc     120
cccggcaagg gcttggagtg ggtcgcccgc atctacccca ccaacggata tacgcgttat     180
gccgatagcg ttaagggccg ctttacgatc tcggcggata ccagcaagaa cacggcttat     240
ctgcagatga actcccttcg ggccgaggat acggccgtgt actactgtag ccgttgggga     300
ggcgatggat tctacgcgat ggattactgg ggacaaggta ccctggtcac agtgtcctcc     360
gccagcacca agggccctag cgtcttcccc ctcgccccaa gcagcaagtc gacctccggc     420
ggcacggcgc ctttgggctg cctcgtcaag gactatttcc ctgaaccagt gacggtcagc     480
tggaactctg gtgcgctcac ttcgggcgtc cacactttcc ccgccgtcct gcagtcgtcg     540
ggtctgtact cgctgtcgag cgttgtcaca gtcccaagca gctcgctcgg tactcagact     600
tatatctgca acgtcaacca caagccctct aacaccaagg tcgacactag ggtggagccg     660
aagtcctgcg ataagacaca cacatgtcca ccctgccccg gccccgagct gctgggcggc     720
ccctccgtct ttctctttcc gcccaagcct aaggacacgt tgatgatttc gcgaacgccg     780
gaggtgacct gtgtcgtcgt cgacgtttcc catgaggatc ctgaggtcaa gtttaactgg     840
tacgtcgacg gcgtcgaggt ccataacgcc aagaccaagc cccgggagga acagtacaat     900
agcacttacc gcgtggtttc tgtcctcacc gtgctgcacc aagattggct taacggaaag     960
gaatacaagt gcaaggtgtc caacaaggca ctgcccgccc ccatcgagaa gactatcagc    1020
aaggcgaagg gccagcctcg ggaaccccaa gtgtataccc ttccgccgtc ccgggaggag    1080
atgaccaaga atcaggtctc cctgacgtgc ctggttaagg gcttctaccc ctctgacatc    1140
gccgtcgagt gggagagcaa tggccagccc gagaacaact acaagaccac gcccccggtc    1200
ctcgacagcg acggcagctt cttcctgtac tccaagctga cggtggacaa gagccgttgg    1260
caacagggaa atgttttttc gtgctcggtc atgcacgagg cgttgcacaa ccactacacg    1320
cagaagtccc tctcgctctc tcccggaaag                                     1350
```

```
<210> SEQ ID NO 90
<211> LENGTH: 1350
<212> TYPE: DNA
<213> ORGANISM: Artificial Sequence
<220> FEATURE:
<223> OTHER INFORMATION: Sequence is synthesized.
```

-continued

<400> SEQUENCE: 90

```
gaggtccagc ttgtcgagag cggcggcggc ctcgtccaac ctggcggatc cctgcggctc        60
agctgcgcgg ctagcggctt caacatcaag gatacgtaca ttcactgggt gcgccaggcc       120
cctggaaagg gcctcgagtg ggtcgctcgg atctacccca cgaacggcta cacccgctac       180
gctgacagcg tcaagggccg cttcaccatt tctgccgaca cgtctaagaa cactgcatac       240
ctccagatga actccttgcg cgccgaggac accgcagtct actactgctc ccgttggggc       300
ggcgacggct tttacgcgat ggactactgg ggtcagggca cactcgtgac agtcagctcc       360
gcctctacca agggccctag cgtgttcccc cttgcccccc cctctaagtc gaccagcggc       420
ggcacagccg ccctcggctg cctcgtcaag gactatttcc ccgaaccggt cacggtcagc       480
tggaactccg gcgcgctcac ttccggcgtg catacctttc ctgccgtcct gcagtcttcc       540
ggcctttact ccttgtcctc cgtcgtcact gtcccctcgt cctcccttgg cacgcagacg       600
tacatttgca acgtcaacca caagccttcg aacacaaagg tcgacacccg cgttgagccc       660
aagtcttgcg acaagaccca tacctgccct ccttgcccag cacccgaact gcttggcgga       720
cccagcgtct ttctgtttcc gccaaagcca aaggacaccc ttatgatttc ccgaacccct       780
gaagtcacgt gcgtcgttgt cgatgtgagc cacgaagatc ccgaagtcaa gtttaactgg       840
tatgtcgacg gcgtcgaggt ccacaacgcc aagacgaagc cccgcgagga gcagtacaac       900
tccacgtacc gcgtggtctc tgtcctcacg gtcctgcatc aggactggct caacggcaag       960
gaatacaagt gtaaggtcag caacaaggct ctgccggccc ctattgagaa gaccatctcc      1020
aaggccaagg gccagccccg cgaaccacaa gtgtacaccc tgcctccctc gcgagaagag      1080
atgacaaaga accaggtcag cttgacctgc cttgttaagg gtttttaccc atcggacatc      1140
gcagtcgagt gggagagcaa tggccagcca gagaacaact acaagaccac gcccctgtc       1200 ctcgacagcg acggaagctt tttcctgtac tctaagctta cagttgacaa gagcaggtgg      1260
cagcagggca cgtcttcag ctgtagcgtg atgcacgaag ctctgcacaa ccactacacc      1320
cagaagtctc ttagcttgag cccgggaaag                                       1350
```

<210> SEQ ID NO 91
<211> LENGTH: 214
<212> TYPE: PRT
<213> ORGANISM: Artificial Sequence
<220> FEATURE:
<223> OTHER INFORMATION: Sequence is synthesized.

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Thr Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 92
<211> LENGTH: 642
<212> TYPE: DNA
<213> ORGANISM: Artificial Sequence
<220> FEATURE:
<223> OTHER INFORMATION: Sequence is synthesized.

<400> SEQUENCE: 92
gacatccaga tgacccagag ccccagcagc ctcagcgcct ctgtcggcga ccgcgtcacc        60
atcacctgcc gcgccagcca ggacgtcaac accgccgtcg cctggtatca gcagaagccc       120
ggcaaggccc ccaagctcct catctacagc gccagcttcc tctacagcgg cgtccccagc       180
cgcttcagcg gcagccgcag cggcaccgac ttcaccctca ccatcagcag cctccagccc       240
gaggacttcg ccacctacta ctgccagcag cactacacca cccccccccac cttcggccag       300 ggcaccaagg tcgagatcac ccgcaccgtc gcggcgccaa gcgtctttat cttccccccc       360
agcgacgagc agctcaagag cggcaccgcc agcgtcgtct gcctcctcaa caacttctac       420
ccccgcgagg ccaaggtcca gtggaaggtc gacaacgccc tccagagcgg caacagccag       480
gagagcgtca ccgagcagga cagcaaggac tccacctaca gcctcagcag caccctcacc       540
ctctccaagg ccgactacga gaagcacaag gtctacgcct gcgaggtcac ccaccagggc       600
ctcagctccc ccgtcaccaa gagcttcaac cgcggcgagt gc                          642

<210> SEQ ID NO 93
<211> LENGTH: 478
<212> TYPE: PRT
<213> ORGANISM: Artificial Sequence
<220> FEATURE:
<223> OTHER INFORMATION: Sequence is synthesized.

<400> SEQUENCE: 93

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80
```

-continued

```
Asn Glu Thr Cys Ala Lys Asn Cys Cys Leu Asp Gly Ala Ala Tyr Ala
            85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro
465                 470                 475
```

```
<210> SEQ ID NO 94
<211> LENGTH: 1565
<212> TYPE: DNA
```

```
<213> ORGANISM: Artificial Sequence
<220> FEATURE:
<223> OTHER INFORMATION: Sequence is synthesized.

<400> SEQUENCE: 94
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct gcgcgaagaa ctgctgtctg gacggtgccg cctacgcgtc cacgtacgga     300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtaagtgac ttaccatgaa     480
cccctgacgc tatcttcttg ttggctccca gctgactggc caattcaagg tgcggcttga     540
acggagctct ctacttcgtg tccatggacg cggatggtgg cgtgagcaag tatcccacca     600
acaccgctgg cgccaagtac ggcacggggt actgtgacag ccagtgtccc cgcgatctga     660
agttcatcaa tggccaggcc aacgttgagg ctgggagcc gtcatccaac aacgcgaaca     720
cgggcattgg aggacacgga agctgctgct ctgagatgga tatctgggag gccaactcca     780
tctccgaggc tcttacccccc cacccttgca cgactgtcgg ccaggagatc tgcgagggtg     840
atgggtgcgg cggaacttac tccgataaca gatatggcgg cacttgcgat cccgatggct     900
gcgactggaa cccataccgc ctgggcaaca ccagcttcta cggccctggc tcaagcttta     960
ccctcgatac caccaagaaa ttgaccgttg tcacccagtt cgagacgtcg ggtgccatca    1020
accgatacta tgtccagaat ggcgtcactt tccagcagcc caacgccgag cttggtagtt    1080
actctggcaa cgagctcaac gatgattact gcacagctga ggaggcagaa ttcggcggat    1140
cctctttctc agacaagggc ggcctgactc agttcaagaa ggctacctct ggcggcatgg    1200
ttctggtcat gagtctgtgg gatgatgtga gtttgatgga caaacatgcg cgttgacaaa    1260
gagtcaagca gctgactgag atgttacagt actacgccaa catgctgtgg ctggactcca    1320
cctacccgac aaacgagacc tcctccacac ccggtgccgt gcgcggaagc tgctccacca    1380
gctccggtgt ccctgctcag gtcgaatctc agtctcccaa cgccaaggtc accttctcca    1440
acatcaagtt cggacccatt ggcagcaccg gcaaccctag cggcggcaac cctcccggcg    1500
gaaacccgcc tggcaccacc accacccgcc gcccagccac taccactgga agctctcccg    1560
gacct                                                                1565
```

FUSION POLYPEPTIDES

CROSS-REFERENCE TO RELATED APPLICATIONS

This application is a U.S. National Stage Application under 35 U.S.C. § 371 of International Patent Application No. PCT/US2020/021685, filed Mar. 9, 2020, which claims priority to U.S. Provisional Patent Application No. 62/815,912, filed Mar. 8, 2019, the disclosure of which are incorporated by reference herein in their entireties.

FIELD OF THE INVENTION

Provided herein, inter alia, are compositions comprising improved cleavable fusion polypeptides as well as methods for utilizing the same to produce one or more polypeptides of interest in a host cell.

BACKGROUND

Production of fusion polypeptides has been reported in a number of organisms including *E. coli*, yeast and filamentous fungi. In some of these fusion proteins, a protease recognition site has been inserted between a polypeptide of interest and a carrier protein (e.g., Contreras et al., 1991, *Biotechnology* (NY), 9(4):378-81 and Ward et al., 1995, *Biotechnology* (NY), 13(5):498-503). However, in many instances, incomplete cleavage has been observed, leading to suboptimal yield of one or more polypeptides of interest. Accordingly, compositions and methods for improved fusion protein production as well as efficient and complete protease-mediated fusion protein cleavage are needed. The subject matter disclosed herein addresses these needs and provides additional benefits as well.

SUMMARY

Provided herein, inter alia, are non-naturally occurring engineered fusion polypeptides with altered amino acid sequences that result in improved or complete protease-mediated (such as, KEX2-mediated) cleavage when producing and purifying one or more polypeptides of interest in a host cell as well as methods for utilizing the same. The disclosed methods, engineered fusion polypeptides, and recombinant host cells provide increased fusion polypeptide secretion and/or purification of one or more polypeptides of interest when compared to fusion polypeptides that do not contain the disclosed altered amino acid sequences and/or that are not used in accordance with the methods disclosed herein. Accordingly, in some aspects, provided herein are fusion polypeptides comprising an amino acid sequence $T_1$-$S_2$-V-$A_3$-$V_4$-$E_5$-$X_1$-$X_2$-$Q_6$-$V_7$-(SEQ ID NO:1), wherein 1) $X_1$ and $X_2$ are basic amino acids; and 2) the amino acid sequence has one or more substitution(s) selected from the group consisting of: $T_1$ substituted with an amino acid selected from the group consisting of a hydrophobic amino acid, an aromatic amino acid, an acidic amino acid, and a basic amino acid; $S_2$ substituted with an amino acid selected from the group consisting of a hydrophobic amino acid, an aromatic amino acid, a basic amino acid, and an amino acid that influences chain orientation; $A_3$ substituted with an amino acid selected from the group consisting of a basic amino acid and M; $V_4$ substituted with L; $E_5$ substituted with an aromatic amino acid; $Q_6$ substituted with an amino acid selected from the group consisting of an acidic amino acid and an amino acid that influences chain orientation; and/or $V_7$ substituted with an amino acid selected from the group consisting of L, I, and an aromatic amino acid. In some embodiments, $T_1$ is substituted with an amino acid selected from the group consisting of A, F, M, Q, R, N, E, and Y; $S_2$ is substituted with an amino acid selected from the group consisting of F, H, K, L, M, P, Q, R, N and V; $A_3$ is substituted with an amino acid selected from the group consisting of H, K, M, and R; $E_5$ is substituted with an amino acid selected from the group consisting of F and W; $Q_6$ is substituted with an amino acid selected from the group consisting of D and G; and/or $V_7$ is substituted with an amino acid selected from the group consisting of L, I, and F.

In some embodiments of any of the embodiments disclosed herein, the amino acid sequence is selected from the group consisting of ASVAVEKRQV (SEQ ID NO:3), FSVAVEKRQV (SEQ ID NO:2), MSVAVEKRQV (SEQ ID NO:4), QSVAVEKRQV (SEQ ID NO:5), RSVAVEKRQV (SEQ ID NO:6), and YSVAVEKRQV (SEQ ID NO:7). In some embodiments of any of the embodiments disclosed herein, the amino acid sequence is selected from the group consisting of TFVAVEKRQV (SEQ ID NO:8), THVAVEKRQV (SEQ ID NO:9), TKVAVEKRQV (SEQ ID NO:10), TLVAVEKRQV (SEQ ID NO:11), TMVAVEKRQV (SEQ ID NO:12), TPVAVEKRQV (SEQ ID NO:13), TQVAVEKRQV (SEQ ID NO:14), TRVAVEKRQV (SEQ ID NO:15), and TVVAVEKRQV (SEQ ID NO:16). In some embodiments of any of the embodiments disclosed herein, the amino acid sequence is selected from the group consisting of TSVHVEKRQV (SEQ ID NO:17), TSVKVEKRQV (SEQ ID NO:18), and TSVRVEKRQV (SEQ ID NO:19). In some embodiments of any of the embodiments disclosed herein, the amino acid sequence TSVALEKRQV (SEQ ID NO:20). In some embodiments of any of the embodiments disclosed herein, the amino acid sequence is selected from the group consisting of TSVAVFKRQV (SEQ ID NO:21) and TSVAVWKRQV (SEQ ID NO:22). In some embodiments of any of the embodiments disclosed herein, the amino acid sequence is selected from the group consisting of TSVAVEKRDV (SEQ ID NO:23) and TSVAVEKRGV (SEQ ID NO:24). In some embodiments of any of the embodiments disclosed herein, the amino acid sequence is selected from the group consisting of TSVAVEKRQF (SEQ ID NO:25) and TSVAVEKRQL (SEQ ID NO:26). In some embodiments of any of the embodiments disclosed herein, the amino acid sequence further comprises an additional two amino acids, $T_8$-$L_9$ (SEQ ID NO:64), on the C-terminus, wherein $T_8$ is substituted with an amino acid selected from the group consisting of an acidic amino acid and a hydrophobic amino acid; and/or $L_9$ is substituted with an amino acid selected from the group consisting of I and V. In some embodiments, $T_8$ is substituted with an E or F. In some embodiments of any of the embodiments disclosed herein, the amino acid sequence is TSVAVEKRQVEL (SEQ ID NO:27). In some embodiments of any of the embodiments disclosed herein, the amino acid sequence is selected from the group consisting of TSVAVEKRQVTI (SEQ ID NO:28) and TSVAVEKRQVTV (SEQ ID NO:29). In some embodiments of any of the embodiments disclosed herein, the fusion polypeptide comprises two or more substitutions. In some embodiments, at least one of the two or more substitutions is at $S_2$ or $V_4$. In some embodiments, the substitution at $S_2$ is an H or an N. In some embodiments, the amino acid is sequence selected from the group consisting of THVAVEKRQVTI (SEQ ID NO:30), THVAVEKRDVTL (SEQ ID NO:31), THVAVEKRQVAL (SEQ ID NO:32), EHVAVEKRQVTL (SEQ ID NO:33), TNVAVEKRDVTL (SEQ ID NO:34), and TNVAVEKRQVAL (SEQ ID NO:35). In some embodiments, the substitution at $V_4$ is an L. In some embodiments, the amino acid sequence is selected from the group consisting of TSVALWKRQVTL (SEQ ID NO:36), TSVMLEKRQVTL (SEQ ID NO:37), TSVALEKRQITL (SEQ ID NO:38) and TSVALEKRQVAL (SEQ ID NO:39). In some embodiments, the fusion polypeptide comprises substitutions at $S_2$ and $V_4$. In some embodiments, the amino acid sequence is THVALEKRQVTL (SEQ ID NO:40). In some embodiments, the amino acid sequence is TSVAVEKRDVAL (SEQ ID NO:41). In some embodiments of any of the embodiments disclosed herein, the fusion polypeptide comprises three or more substitutions. In some embodiments, the amino acid sequence is selected from the group consisting of THVMLEKRQVTL (SEQ ID NO:42), TKVMLEKRQVTL (SEQ ID NO:43), THVAVEKRDVAL (SEQ ID NO:44), THVALWKRQVTL (SEQ ID NO:45), TKVAVEKRDLTL (SEQ ID NO:46), TNVAVEKRDLTL (SEQ ID NO:47), EHVAVWKRQVTL (SEQ ID NO:48), EHVALEKRQVTL (SEQ ID NO:49), ESVALWKRQVTL (SEQ ID NO:50), RSVRVEKRDVTL (SEQ ID NO:51), and TSVALEKRDVAL (SEQ ID NO:52). In some embodiments of any of the embodiments disclosed herein, the fusion polypeptide comprises four or more substitutions. In some embodiments, the amino acid sequence is selected from the group consisting of THVALEKRDVAL (SEQ ID NO:53), TKVRVEKRDLTL (SEQ ID NO:54), TNVALEKRDVAL (SEQ ID NO:55), EHVALWKRQVTL (SEQ ID NO:56), EPVALWKRQVTL (SEQ ID NO:57), NHVALWKRQVTL (SEQ ID NO:58), RSVRVEKRDLTL (SEQ ID NO:59), RKVRVEKRDVTL (SEQ ID NO:60), RKVRVEKRQLTL (SEQ ID NO:61), and RKVAVEKRDLTL (SEQ ID NO:62). In some embodiments of any of the embodiments disclosed herein, the fusion polypeptide comprises five or more substitutions. In some embodiments, the amino acid sequence is RKVRVEKRDLTL (SEQ ID NO:63). In some embodiments of any of the embodiments disclosed herein, $X_1$ and $X_2$ are selected from the group consisting of KK, RR, KR, and RK. In some embodiments of any of the embodiments disclosed herein, the amino acid sequence is completely cleaved by one or more protease(s). In some embodiments, the protease is a Kex2 serine peptidase (EC 3.4.21.61). In some embodiments of any of the embodiments disclosed herein, the fusion polypeptide further comprises a polypeptide encoding a signal sequence. In some embodiments, the polypeptide encoding a signal sequence is located N-terminal or C-terminal from the amino acid sequence of SEQ ID NO:1. In some embodiments of any of the embodiments disclosed herein, the fusion polypeptide further comprises a polypeptide encoding a carrier protein. In some embodiments, the polypeptide encoding a carrier protein is located N-terminal or C-terminal from the amino acid sequence of SEQ ID NO:1. In some embodiments of any of the embodiments disclosed herein, the polypeptide encoding a carrier protein is adjacent to the polypeptide encoding a signal sequence. In some embodiments of any of the embodiments disclosed herein, the carrier protein comprises CBH1 or a fragment thereof. In some embodiments of any of the embodiments disclosed herein, the fusion polypeptide further comprises a polypeptide of interest. In some embodiments, the polypeptide encoding a polypeptide of interest is located N-terminal or C-terminal from the amino acid sequence of SEQ ID NO:1. In some embodiments of any of the embodiments disclosed herein, the polypeptide of interest is an enzyme. In some embodiments, the enzyme is an enzyme selected from the group consisting of active or inactive carbohydrate degrading enzymes, proteases, lipases, and cell lysing enzymes. In some embodiments of any of the embodiments disclosed herein, the polypeptide of interest is a therapeutic protein. In some embodiments, the therapeutic protein is an antibody or functional fragment thereof. In some embodiments, the antibody is a light chain or heavy chain monoclonal antibody. In some embodiments of any of the embodiments disclosed herein, the signal sequence is a CBH1 signal sequence, the carrier protein is a CBH1-containing carrier protein, and the polypeptide of interest is an antibody light chain or functional fragment thereof. In some embodiments of any of the embodiments disclosed herein, the signal sequence is a CBH1 signal sequence, the carrier protein is a CBH1-containing carrier protein, and the polypeptide of interest is an antibody heavy chain or functional fragment thereof. In some embodiments of any of the embodiments disclosed herein, the signal sequence is a CBH1 signal sequence, the carrier protein is a CBH1-containing carrier protein, and the polypeptide of interest is an antibody heavy chain or fragment thereof and an antibody light chain or functional fragment thereof. In some embodiments, the antibody or functional fragment thereof is a single-domain antibody (sdAb). In some embodiments, the antibody or functional fragment thereof is selected from the group consisting of a Fv, a Fab, a Fab', a Fab'-SH, a F(ab')$_2$, a diabody, a linear antibody, a single-chain antibody molecule (e.g. scFv), and a multispecific antibody formed from antibody fragments. In some embodiments of any of the embodiments disclosed herein, the antibody or functional fragment thereof is an anti-Respiratory Syncytial Virus (RSV) antibody, an anti-ebola virus antibody, an anti-aggregated β-amyloid (Aβ) antibody, an anti-human immunodeficiency virus (HIV) antibody, an anti-herpes simplex virus (HSV) antibody, an anti-sperm antibody (such as an anti-human contraceptive antigen (HCA) antibody), and anti-HER2/neu antibody.

In other aspects, provided herein is a nucleic acid encoding any of the fusion polypeptides disclosed herein.

In further aspects, provided herein is a vector encoding any of the nucleic acids disclosed herein. In some embodiments, the vector further comprises a nucleic acid sequence encoding a promoter.

In yet other aspects, provided herein are host cells comprising any of the fusion polypeptides disclosed herein, any of the nucleic acids disclosed herein, and/or any of the vectors disclosed herein. In some embodiments, the host cell is selected from the group consisting of a mammalian host cell, a bacterial host cell, and a fungal host cell. In some embodiments, the mammalian cell is a Chinese Hamster Ovary (CHO) cell. In some embodiments, the bacterial cell is an *E. coli* cell. In some embodiments, the fungal cell is a yeast cell or a filamentous fungal cell. In some embodiments, the yeast cell is a *Saccharomyces* sp. In some embodiments of any of the embodiments disclosed herein, the fungal cell is selected from the group consisting of a *Trichoderma* sp., a *Penicillium* sp., a *Humicola* sp., a *Chrysosporium* sp., a *Gliocladium* sp., an *Aspergillus* sp., a *Fusarium* sp., a *Mucor* sp., a *Neurospora* sp., a Hypocrea sp.; *Myceliophthora* sp., and an *Emericella* sp. In some embodiments, the fungal cell is selected from the group consisting of *Trichoderma reesei, Trichoderma viride, Trichoderma koningii, Trichoderma harzianum, Humicola insolens, Humicola grisea, Chrysosporium lucknowense, Aspergillus oryzae, Aspergillus niger, Aspergillus nidulans, Aspergillus kawachi, Aspergillus aculeatus, Aspergillus japonicus, Aspergillus sojae, Myceliophthora thermophila,* and *Aspergillus awamori.*

In other aspects, provided herein are methods for producing any of the fusion polypeptides disclosed herein comprising: culturing any of the host cells disclosed herein under suitable conditions for the production of the fusion polypeptide. In some embodiments, the method further comprises isolating the fusion polypeptide. In some embodiments of any of the embodiments disclosed herein, the method further comprises cleaving the fusion polypeptide with a protease. In some embodiments, the protease is a Kex2 serine peptidase (EC 3.4.21.61). In some embodiments of any of the embodiments disclosed herein, cleavage of the fusion polypeptide is increased compared to the cleavage of an equivalent fusion polypeptide lacking the amino acid sequence of SEQ ID NO:1. In some embodiments, the method further comprises isolating one or both of the products of the cleaved fusion polypeptide. In some embodiments of any of the embodiments disclosed herein, secretion of the fusion polypeptide is increased compared to the secretion of an equivalent fusion polypeptide lacking the amino acid sequence of SEQ ID NO:1.

In additional aspects, provided herein are methods for cleaving a fusion polypeptide comprising: contacting any of the fusion polypeptides disclosed herein with a protease. In some embodiments, the protease is a Kex2 serine peptidase (EC 3.4.21.61).

In other aspects, provided herein are kits comprising a) written instructions for producing any of the fusion polypeptides disclosed herein; and b) one or more of any of the nucleic acids disclosed herein; 2) any of the vectors disclosed herein; and/or 3) any of the host cells disclosed herein. In some embodiments, the kit further comprises one or more of 4) a composition comprising a Kex2 serine peptidase (EC 3.4.21.61); and/or 5) a nucleic acid encoding a Kex2 serine peptidase. In some embodiments of any of the embodiments disclosed herein, the kit further comprises a host cell that expresses a Kex2 serine peptidase. In some embodiments of any of the embodiments disclosed herein, the kit further comprises one or more of 6) a composition comprising an additional protease; and/or 7) a nucleic acid encoding an additional protease.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF DESCRIPTION OF THE DRAWINGS

FIG. 5A depicts the nucleotide sequence of the Synagis antibody heavy chain. FIG. 5B depicts the amino acid sequence of the Synagis antibody heavy chain.

FIG. 10A depicts the amino acid sequence of the trastuzumab HC. FIG. 10B depicts the nucleotide sequence of the trastuzumab HC in pJC159. FIG. 10C depicts the nucleotide sequence of the trastuzumab HC in pJC158.

FIG. 11A depicts the amino acid sequence of the trastuzumab LC. FIG. 11B depicts the nucleotide sequence of the trastuzumab LC.

FIG. 12A depicts the amino acid sequence of CBH1. FIG. 12B depicts the nucleotide sequence of CBH1.

DETAILED DESCRIPTION

Figure 1:
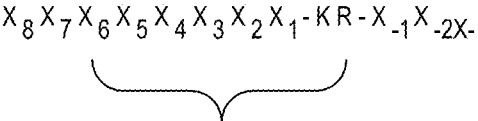
FIG. 1 is a schematic depicting a fusion polypeptide, including KEX2 site pre- and post-sequences.

The invention disclosed herein is based, in part, on the inventors' observations that protein secretion and/or protein cleavage is enhanced in a fusion polypeptide when a protease recognition site is engineered to include one or more alternative substituted amino acids in the protease recognition site pre-sequence and/or post-sequence.

Accordingly, provided herein are fusion DNA constructs, vectors, fusion polypeptides, host cells expressing a fusion DNA construct and/or fusion polypeptide, as well as methods for enhancing the secretion and/or cleavage of a fusion polypeptide made in a host cell. More specifically, and in some non-limiting aspects, engineered KEX2 site pre- and/or post-sequences have been included in a fusion polypeptide to enhance or improve cleavage of a polypeptide of interest from the fusion polypeptide. The fusion polypeptides disclosed herein exhibit better secretion and/or purification of polypeptides of interest compared to fusion polypeptides that do not include the engineered protease recognition site pre- and/or post-sequences disclosed herein. As such, the instant disclosure provides alternative and improved methods for protein production, particularly therapeutic protein production, such as antibody production, which result in relatively quick scale-up time and high levels of purified protein with limited risk of contamination by uncleaved product.

I. Definitions

The term "polypeptide" or "protein" is meant to refer to any polymer containing any of the 20 natural amino acids regardless of its size. Although the term "protein" is often used in reference to relatively large proteins, and "peptide" is often used in reference to small polypeptides, use of these terms in the field often overlaps. The term "polypeptide" thus refers generally to proteins, polypeptides, and peptides unless otherwise noted. The conventional one-letter or three-letter code for amino acid residues is used herein.

"Fusion polypeptide" or "fusion protein", as used herein, shall mean a polypeptide comprising two or more different polypeptides or active fragments thereof that are not naturally present in the same polypeptide. In some embodiments, the two or more different polypeptides are operatively linked together covalently, e.g., chemically linked or fused in frame by a peptide bond.

The term "protease recognition site" refers to a cleavage motif in a polypeptide amino acid sequence that is cleaved by a protease.

The term "protease recognition site pre-sequence" refers to the two to six contiguous amino acids [(X)$_n$ where n is 2 to 6] immediately preceding (i.e., immediately N-terminal to) the protease recognition site.

The term "protease recognition site post-sequence" refers to the two to six contiguous amino acids [(X)$_n$ where n is 2 to 6] immediately following (i.e., immediately C-terminal to) the protease recognition site.

The term "KEX2" refers to a calcium-dependent endopeptidase having an activity defined as EC 3.4.21.61, according to IUBMB Enzyme Nomenclature. KEX2 cleaves a peptide bond (the KEX2 cleavage site) that is immediately C-terminal to a pair of basic amino acids during protein secretion.

The term "KEX2 region" refers to a contiguous four to twelve amino acid residue region (such as any of 4, 5, 6, 7, 8, 9, 10, 11, or 12 amino acids) which is located in a polypeptide, for example, a fusion polypeptide. The KEX2 region is comprised of a KEX2 site, a KEX2 site pre-sequence, and a KEX2 site post-sequence.

The term "KEX2 site" refers to a two amino acid KEX2 protease recognition site cleavage motif in a polypeptide. A KEX2 site contains two contiguous basic amino acids (e.g., lysine, histidine and/or arginine) in any order, (e.g., KK, RR, KR or RK).

The term "KEX2 site pre-sequence" refers to the two to eight contiguous amino acids [(X)$_n$ where n is 2 to 8, such as any of 2, 3, 4, 5, 6, 7, or 8] immediately preceding (i.e., immediately N-terminal to) the KEX2 site. For example, if a KEX2 region is defined as TSVAVEKRQV (SEQ ID NO:80), the "KR" motif is the KEX2 site of the region; n is 6 and the "TSVAVE" motif (SEQ ID NO:81) corresponds to the KEX2 site pre-sequence of the region.

The term "KEX2 site post-sequence" refers to the one or two, or in other embodiments, one to four, contiguous amino acids [(X)$_n$ where n is 1 to 4, such as any of 1, 2, 3, or 4] immediately following (i.e., immediately C-terminal to) the KEX2 site. For example, if a KEX2 region is defined as TSVAVEKRQV (SEQ ID NO:80), the "KR" motif is the KEX2 site of the region; n is 2 and the "QV" motif corresponds to the KEX2 site post-sequence of the region.

The term "nucleic acid" or "polynucleotide" encompasses DNA, RNA, single stranded or double stranded and chemical modifications thereof. The terms "nucleic acid" and "polynucleotide" can be used interchangeably herein. Because the genetic code is degenerate, more than one codon can be used to encode a particular amino acid, and the present subject matter encompasses polynucleotides, which encode a particular amino acid sequence.

"The terms "wild-type," "wildtype," "parental," or "reference," with respect to a polypeptide, refer to a naturally-occurring polypeptide that does not include a man-made substitution, insertion, or deletion at one or more amino acid positions. Similarly, the term "wild-type," "wildtype," "parental," or "reference," with respect to a polynucleotide, refers to a naturally-occurring polynucleotide that does not include a man-made nucleoside change. However, a polynucleotide encoding a wild-type, parental, or reference polypeptide is not limited to a naturally-occurring polynucleotide, but rather encompasses any polynucleotide encoding the wild-type, parental, or reference polypeptide.

As used herein, the term "non-naturally occurring" refers to anything that is not found in nature (e.g., recombinant nucleic acids and protein sequences produced in the laboratory), such as the modification of a wild-type nucleic acid and/or amino acid sequence. In some embodiments, a non-naturally occurring polypeptide contains an amino acid substitution (i.e. a mutation) that is not found in a corresponding wild-type or naturally-occurring amino acid sequence.

As used herein, a "derivative" or "variant" of a polypeptide means a polypeptide, which is derived from a precursor polypeptide (e.g., the native polypeptide) by addition of one or more amino acids to either or both the C- and N-terminal end, substitution of one or more amino acids at one or a number of different sites in the amino acid sequence, deletion of one or more amino acids at either or both ends of the polypeptide or at one or more sites in the amino acid sequence, or insertion of one or more amino acids at one or more sites in the amino acid sequence.

As used herein, a "variant polynucleotide" encodes a variant polypeptide, has a specified degree of homology/identity with a parent polynucleotide, or hybridized under stringent conditions to a parent polynucleotide or the complement thereof. Suitably, a variant polynucleotide has at least 80%, at least 85%, at least 90%, at least 91%, at least 92%, at least 93%, at least 94%, at least 95%, at least 96%, at least 97%, at least 98%, or even at least 99% nucleotide sequence identity to a parent polynucleotide or to a complement of the parent polynucleotide. Methods for determining percent identity are known in the art.

The term "derived from" encompasses the terms "originated from," "obtained from," "obtainable from," "isolated from," and "created from," and generally indicates that one specified material finds its origin in another specified material or has features that can be described with reference to another specified material.

"Control sequence" is defined herein to include all components, which are necessary or advantageous for the expression of a polynucleotide or polypeptide of interest. Each control sequence can be native or foreign to the nucleic acid sequence encoding a polypeptide. Such control sequences include, but are not limited to, a leader sequence, polyadenylation sequence, propeptide sequence, promoter, signal peptide sequence, and transcription terminator. At a minimum, the control sequences include a promoter, and transcriptional and translational stop signals. The control sequences can be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed in a functional relationship (i.e., at a position relative to) with a polynucleotide or polypeptide of interest, such as the coding sequence in the DNA sequence, such that the control sequence directs or regulates the expression of a polynucleotide and/or polypeptide.

The term "DNA construct" means a DNA sequence which is operably linked to a suitable control sequence capable of effecting expression of a protein in a suitable host. Such control sequences can include a promoter to effect transcription, an optional operator sequence to control transcription, a sequence encoding suitable ribosome binding sites on the mRNA, enhancers and sequences which control termination of transcription and translation.

The term "fusion DNA construct" or "fusion nucleic acid" refers to a nucleic acid which comprises from 5' to 3' a number of polynucleotide sequences (e.g. and without limitation, a DNA molecule encoding a signal sequence, a DNA molecule encoding a carrier protein, a DNA molecule coding for a KEX2 site and a DNA molecule encoding a polypeptide of interest) operably linked together and which encode a fusion polypeptide.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a vector that has the ability to incorporate and express a DNA fragment in a cell. Many prokaryotic and eukaryotic expression vectors are commercially available.

"Promoter" or "promoter sequence" is a nucleic acid sequence that is recognized by a host cell for expression of a polynucleotide of interest, such as a coding region. Generally, the promoter sequence contains transcriptional control sequences, which mediate the expression of a polynucleotide of interest. The promoter can be any nucleic acid sequence which shows transcriptional activity in the host cell of choice, including mutant, truncated, and hybrid promoters, and can be obtained from genes encoding extracellular or intracellular polypeptides either homologous or heterologous to the host cell.

The term "signal sequence" refers to a sequence of amino acids at the amino terminus of a protein that directs the protein to the secretion system for secretion from a cell. The signal sequence is cleaved from the protein prior to secretion of the protein. In certain cases, a signal sequence can be referred to as a "signal peptide" or "leader peptide". The definition of a signal sequence is a functional one. The mature form of the extracellular protein lacks the signal sequence which is cleaved off during the secretion process.

The term "carrier protein" as used herein refers to proteins that function to or facilitate the secretion of polypeptides (such as, fusion polypeptides) from a host cell. Exemplary carrier proteins are discussed in more detail below.

The term "recombinant," when used in reference to a subject cell, nucleic acid, polypeptides/enzymes or vector, indicates that the subject has been modified from its native state. Thus, for example, recombinant cells express genes that are not found within the native (non-recombinant) form of the cell, or express native genes at different levels or under different conditions than found in nature. Recombinant nucleic acids can differ from a native sequence by one or more nucleotides and/or are operably linked to heterologous sequences, e.g., a heterologous promoter, signal sequences that allow secretion, etc., in an expression vector. Recombinant polypeptides/enzymes can differ from a native sequence by one or more amino acids and/or are fused with heterologous sequences. A vector comprising a nucleic acid encoding an antibody heavy chain is, for example, a recombinant vector.

As used herein, "microorganism" refers to a bacterium, a fungus, a virus, a protozoan, and other microbes or microscopic organisms.

"Host strain" or "host cell" means a suitable host for an expression vector or DNA construct comprising a polynucleotide encoding a polypeptide and particularly a recombinant fusion polypeptide encompassed by the present disclosure. In specific embodiments, the host strains can be a filamentous fungal cell or a mammalian cell. The term "host cell" includes both cells and protoplasts.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, glucans, and other complex polysaccharides. The filamentous fungi disclosed herein are morphologically, physiologically, and genetically distinct from yeasts. Vegetative growth by filamentous fungi is by hyphal elongation and carbon catabolism is obligatory aerobic.

The term "culturing" refers to growing a population of microbial cells under suitable conditions in a liquid or solid medium.

The term "heterologous" with reference to a polynucleotide or polypeptide refers to a polynucleotide or polypeptide that does not naturally occur in a host cell. In some embodiments, the protein is a commercially important industrial protein and in some embodiments, the heterologous protein is a therapeutic protein. It is intended that the term encompass proteins that are encoded by naturally occurring genes, mutated genes, and/or synthetic genes.

The term "homologous" with reference to a polynucleotide or protein refers to a polynucleotide or protein that occurs naturally in the host cell.

The terms "recovered," "isolated," and "separated," as used herein, refer to a protein (for example, a polypeptide of interest), cell, nucleic acid or amino acid that is removed from at least one component with which it is associated.

As used herein, the terms "transformed", "stably transformed" and "transgenic" used in reference to a cell means the cell has a non-native (e.g., heterologous) nucleic acid sequence or additional copy of a native (e.g., homologous) nucleic acid sequence integrated into its genome or has an episomal plasmid that is maintained through multiple generations.

As used herein, the term "expression" refers to the process by which a polypeptide is produced based on the nucleic acid sequence of a gene. The process includes both transcription and translation.

The term "secreted protein" refers to a region of a polypeptide that is released from a cell during protein secretion. In some embodiments, the secreted protein is the protein that is released or cleaved from a recombinant fusion polypeptide.

The term "secretion" refers to the selective movement of a protein across a membrane in a host cell to the extracellular space and surrounding media.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, in connection with a numerical value, the term "about" refers to a range of −10% to +10% of the numerical value, unless the term is otherwise specifically defined in context.

As used herein, the singular terms "a," "an," and "the" include the plural reference unless the context clearly indicates otherwise.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is also noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) can further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless defined otherwise herein, all technical and scientific terms used herein have the same meaning as commonly understood by one of ordinary skill in the art to which this invention pertains.

Other definitions of terms may appear throughout the specification.

II. Compositions

A. Fusion Polypeptides

Provided herein are non-naturally occurring fusion polypeptides, fragments thereof, or variants thereof having improved expression and/or cleavage properties. Subject fusion polypeptides can include, without limitation, one or more of a) a signal sequence; b) a carrier protein; c) a protease recognition region comprising: i) a protease cleavage site; ii) a protease cleavage site pre-sequence immediately N-terminal to the protease cleavage site; and/or iii) a protease cleavage site post-sequence immediately C-terminal to the protease cleavage site; and d) one or more polypeptide of interest (such as, without limitation, an antibody heavy chain or light chain). In some embodiments, the protease cleavage site is a KEX2 protease cleavage site, including KEX2 protease cleavage pre- and/or post-cleavage sites.

FIG. 1 illustrates a representative fusion polypeptide. The various parts of a subject polypeptide (i.e., "signal sequence", carrier protein, "linker" (containing the protease recognition sequence) and "desired protein" (i.e. "polypeptide of interest") are so labeled solely for clarity and convenience. It is recognized that the fusion polypeptide can also be referred to as a "pro-protein" or "precursor protein" because it generally contains an N-terminal region that is cleaved off during secretion and a C-terminal region that is secreted.

1. Signal Sequences

The signal sequence of a subject fusion polypeptide can be any signal sequence that facilitates protein secretion from a host cell (e.g., a filamentous fungal host cell). In particular embodiments, the fusion polypeptide can comprise a signal sequence for a protein that is known to be highly secreted from a host cell in which the fusion protein is to be produced. The signal sequence employed can be endogenous or non-endogenous to the host cell in which the fusion polypeptide is to be produced.

Suitable signal sequences are known in the art (see, e.g., Ward et al, Bio/Technology 1990 8:435-440; and Paloheimo et al, *Applied and Environmental Microbiology* 2003 69: 7073-7082). Non-limiting examples of suitable signal sequences include those of cellobiohydrolase I, cellobiohydrolase II, endoglucanases I, II and III, α-amylase, aspartyl proteases, glucoamylase, phytase, mannanase, α and β glucosidases, bovine chymosin, human interferon and human tissue plasminogen activator and synthetic consensus eukaryotic signal sequences such as those described by Gwynne et al., (1987) *Bio/Technology* 5:713-719.

In some embodiments, if *Trichoderma* (e.g. *T. reesei*) is employed as a host cell, the signal sequence or carrier of *T. reesei* mannanase I (Man5A, or MANI), *T. reesei* cellobiohydrolase II (Cel6A or CBHII), endoglucanase I (Cel7b or EGI), endoglucanase II (Cel5a or EGII), endoglucanase III (Cel12A or EGIII), xylanases I or II (XynIIa or XynIIb) or *T. reesei* cellobiohydrolase I (Cel7a or CBHI) can be employed in the fusion polypeptide.

In other embodiments, if an *Aspergillus* (e.g. *A. niger*) is employed as a host cell, the signal sequence or carrier of *A. niger* glucoamylase (GlaA) or alpha amylase can be employed in the fusion polypeptide. *Aspergillus niger* and *Aspergillus awamori* glucoamylases have identical amino acid sequences. Two forms of the enzyme are generally recognized in culture supernatants. GAI is the full-length form (amino acid residues 1-616) and GAII is a natural proteolytic fragment comprising amino acid residues 1-512. GAI is known to fold as two separate domains joined by an extended linker region. The two domains are the 471 residue catalytic domain (amino acids 1-471) and the 108 residue starch binding domain (amino acids 509-616), the linker region between the two domains being 36 residues (amino acids 472-508). GAII lacks the starch binding domain. Reference is made to Libby et al., (1994) *Protein Engineering* 7:1109-1114. In some embodiments, the glucoamylase which is used as a carrier protein and including a signal sequence will have greater than 95%, 96%, 97%, 98% and 99% sequence identity with a catalytic domain of an *Aspergillus* or *Trichoderma* glucoamylase. The term "catalytic domain" refers to a structural portion or region of the amino acid sequence of a protein which possess the catalytic activity of the protein.

2. Carriers

In particular embodiments, the fusion polypeptide can comprise a "carrier protein" that functions to or facilitates the secretion of polypeptides from a host cell.

The carrier protein can include all or part of the mature sequence of a secreted polypeptide. In some embodiments, full length secreted carrier protein polypeptides are used. However, functional portions of secreted carrier protein polypeptides can be employed. As used herein "portion" of a secreted carrier protein polypeptide or grammatical equivalents means a truncated secreted carrier protein polypeptide that retains its ability to fold into a normal, albeit truncated, configuration.

In general, if the carrier protein is a truncated protein, it is C-terminally truncated (i.e., contains an intact N-terminus). Alternatively, the carrier protein can be N-terminally truncated, or optionally truncated at both ends to leave a functional portion. Generally, such portions of a secreted protein which comprise a carrier protein comprise greater than 50%, greater than 70%, greater than 80% and greater than 90% of the secreted protein and, in some embodiments, the N-terminal portion of the secreted protein. In some embodiments, the carrier protein will include a linker region in addition to the catalytic domain. In some embodiments, a portion of the linker region of the CBHI protein can be used in the carrier protein.

In some embodiments, the first amino acid sequence comprising a signal sequence functional as a secretory sequence is encoded by a first DNA molecule. The second amino acid sequence comprising the carrier protein is encoded by a second DNA sequence. However, as described above the signal sequence and the carrier protein can be obtained from the same gene.

3. KEX2 Region

During protein secretion in a fungal cell, certain proteins are cleaved by KEX2, a member of the KEX2 or "kexin" family of serine peptidase (EC 3.4.21.61). KEX2 is a highly specific calcium-dependent endopeptidase that cleaves the peptide bond that is immediately C-terminal to a pair of basic amino acids (i.e., the "KEX2 site") in a protein substrate during secretion of that protein. KEX2 proteins generally contain a cysteine residue near the histidine residue of its active site and are inhibited by p-mercuribenzoate. The founding member of this group, the KEX2 peptidase of *S. cerevisiae* (Fuller et al., 1989, *Proc. Natl. Acad. Sci. USA* 86:1434-1438), cleaves the α-factor pheromone and killer toxin precursors during their secretion.

In some embodiments, the protease recognition site is a KEX2 region. The KEX2 region comprises a KEX2 site $(X_1-X_2)$, a KEX2 site pre-sequence $(X_n=2-6$, such as any of 2, 3, 4, 5, or 6) immediately N-terminal to said KEX2 site, and a KEX2 site pre-sequence $(X_n=2-4$, such as any of 2, 3, or 4) immediately C-terminal to said KEX2 site. In some embodiments, the KEX2 region provides means for cleavage (i.e., separation) at the amino terminus of the polypeptide of interest from the fusion polypeptide in vivo. The KEX2 region of a fusion polypeptide as disclosed herein is not a naturally occurring region between the carrier protein and the polypeptide of interest.

The KEX2 cleavage site can be cleaved by a native filamentous fungal protease (e.g. a native *Aspergillus* KEXB-like protease or native *Trichoderma* KEX2 protease) or can be cleaved by one or more other proteases present in eukaryotic (such as yeast or mammalian) cells. The polypeptide of interest is cleaved from a fusion polypeptide immediately downstream (i.e. C-terminal) of the KEX2 cleavage site.

The KEX2 site contains amino acid sequence "$X_1-X_2$" wherein $X_1$ and $X_2$, are independently, basic amino acids. The KEX2 site can include any one of KK, KR, RK or RR. In one embodiments, the KEX2 site is KR.

The KEX2 site pre-sequence can include amino acid sequence $X_n=2-8$, wherein X is any amino acid and n is 2 to 8, such as any of 2, 3, 4, 5, 6, 7, or 8. The KEX2 region as defined herein is not found naturally in the carrier protein at the C-terminus of the carrier protein in the fusion polypeptides disclosed herein. In some embodiments, the KEX2 site pre-sequence is an amino acid sequence that is different from the naturally occurring contiguous $X_n=2-8$ amino acid residues on the C-terminus of the carrier protein. However, the contiguous $X_n=2-6$ amino acid residues can be found in other parts of the carrier protein and can be linked with a KEX2 site $(X_1-X_2)$, but the KEX2 region will not be attached to the N-terminus of the polypeptide of interest.

Amino acid substitutions in the KEX2 site pre- and/or post-sequence can be the result of replacing one amino acid with another amino acid having similar structural and/or chemical properties, such as the replacement of a leucine with a serine, i.e., conservative substitutions or the result of replacing one amino acid with another amino acid having different structural or chemical properties, such as the replacement of an asparagine with an aspartic acid, i.e., non-conservative substitutions. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Non-conservative substitutions entail exchanging a member of one of these classes for another class. Such substituted residues also can be introduced into the conservative substitution sites or into non-conserved sites.

In some embodiments, when the KEX2 site pre-sequence is defined as $T_1-S_2-V-A_3-V_4-E_5-X_1-X_2$, $T_1$ is substituted with a hydrophobic amino acid, an aromatic amino acid, an acidic amino acid, or a basic amino acid; $S_2$ is substituted with a hydrophobic amino acid, an aromatic amino acid, a basic amino acid, or an amino acid that influences chain orientation; $A_3$ is substituted with a basic amino acid or M; $V_4$ is substituted with L; and/or $E_5$ is substituted with an aromatic amino acid.

In other embodiments, when the KEX2 site post-sequence is defined as $X_1-X_2-Q_6-V_7$, $Q_6$ is substituted with an acidic amino acid or an amino acid that influences chain orientation; and/or $V_7$ is substituted with L, I, or an aromatic amino acid.

In additional embodiments, the KEX2 region is selected from ASVAVEKRQV (SEQ ID NO:3), FSVAVEKRQV (SEQ ID NO:2), MSVAVEKRQV (SEQ ID NO:4), QSVA-VEKRQV (SEQ ID NO:5), RSVAVEKRQV (SEQ ID NO:6), YSVAVEKRQV (SEQ ID NO:7), TFVAVEKRQV (SEQ ID NO:8), THVAVEKRQV (SEQ ID NO:9), TKVA-VEKRQV (SEQ ID NO:10), TLVAVEKRQV (SEQ ID NO:11), TMVAVEKRQV (SEQ ID NO:12), TPVA-VEKRQV (SEQ ID NO:13), TQVAVEKRQV (SEQ ID NO:14), TRVAVEKRQV (SEQ ID NO:15), TVVA-VEKRQV (SEQ ID NO:16), TSVHVEKRQV (SEQ ID NO:17), TSVKVEKRQV (SEQ ID NO:18), TSVRVEKRQV (SEQ ID NO:19), TSVALEKRQV (SEQ ID NO:20), TSVAVFKRQV (SEQ ID NO:21), TSVA-VWKRQV (SEQ ID NO:22), TSVAVEKRDV (SEQ ID NO:23), TSVAVEKRGV (SEQ ID NO:24), TSVAVEKRQF (SEQ ID NO:25), or TSVAVEKRQL (SEQ ID NO:26).

When creating variants with multiple substitutions in the KEX2 region (such as any of 2, 3, 4, or 5 substitutions), the KEX2 site post-sequence can, in additional embodiments, be defined as $X_1-X_2-Q_6-V_7-T_8-L_9$, (SEQ ID NO:64) where $Q_6$ is substituted with an acidic amino acid or an amino acid that influences chain orientation; $V_7$ is substituted with L, I, or an aromatic amino acid; $T_8$ is substituted with an acidic amino acid or a hydrophobic amino acid; and/or $L_9$ is substituted with I or V. In some embodiments, the KEX2 region is selected from TSVAVEKRQVEL (SEQ ID NO:27), TSVA-VEKRQVTI (SEQ ID NO:28), or TSVAVEKRQVTV (SEQ ID NO:29).

In further embodiments when creating variants with multiple substitutions in the KEX2 region (such as any of 2, 3, 4, or 5 substitutions), the KEX2 site pre-sequence can, in additional embodiments, be defined as $G_{-2}-P_{-1}-T_1-S_2-V-A_3-V_4-E_5-X_1-X_2$ (SEQ ID NO:65), where $G_{-2}$ is substituted with a tyrosine and/or $P_{-1}$ is substituted with a threonine or a leucine.

In additional embodiments, the KEX2 region has two or more substitutions (such as any of 2, 3, 4, or 5 substitutions)

compared to an unaltered KEX2 region amino acid sequence selected from THVAVEKRQVTI (SEQ ID NO:30), THVA-VEKRDVTL (SEQ ID NO:31), THVAVEKRQVAL (SEQ ID NO:32), EHVAVEKRQVTL (SEQ ID NO:33), TNVA-VEKRDVTL (SEQ ID NO:34), TNVAVEKRQVAL (SEQ ID NO:35), TSVALWKRQVTL (SEQ ID NO:36), TSVM-LEKRQVTL (SEQ ID NO:37), TSVALEKRQITL (SEQ ID NO:38), TSVALEKRQVAL (SEQ ID NO:39), THVALEKRQVTL (SEQ ID NO:40), TSVAVEKRDVAL (SEQ ID NO:41) THVMLEKRQVTL (SEQ ID NO:42), TKVMLEKRQVTL (SEQ ID NO:43), THVAVEKRDVAL (SEQ ID NO:44), THVALWKRQVTL (SEQ ID NO:45), TKVAVEKRDLTL (SEQ ID NO:46), TNVAVEKRDLTL (SEQ ID NO:47), EHVAVWKRQVTL (SEQ ID NO:48), EHVALEKRQVTL (SEQ ID NO:49), ESVALWKRQVTL (SEQ ID NO:50), RSVRVEKRDVTL (SEQ ID NO:51), TSVALEKRDVAL (SEQ ID NO:52), THVALEKRDVAL (SEQ ID NO:53), TKVRVEKRDLTL (SEQ ID NO:54), TNVALEKRDVAL (SEQ ID NO:55), EHVALWKRQVTL (SEQ ID NO:56), EPVALWKRQVTL (SEQ ID NO:57), NHVALWKRQVTL (SEQ ID NO:58), RSVRVEKRDLTL (SEQ ID NO:59), RKVRVEKRDVTL (SEQ ID NO:60), RKVRVEKRQLTL (SEQ ID NO:61), RKVAVEKRDLTL (SEQ ID NO:62), RKVRVEKRDLTL (SEQ ID NO:63), YLTSVMLEKRQV (SEQ ID NO:83), YLTHVMLEKRQV (SEQ ID NO:84), YPTHVMLEKRQV (SEQ ID NO:85), YPTHVALEKRQV (SEQ ID NO:86), GLTSVMVEKRQV (SEQ ID NO:87), or GLTHVMLEKRQV (SEQ ID NO:88).

In yet other embodiments, the KEX2 site pre-sequence is not KSRS (SEQ ID NO:66); SRIS (SEQ ID NO:67); GGGS (SEQ ID NO:68); TSTY (SEQ ID NO:69); ASIS (SEQ ID NO:70); ATAS (SEQ ID NO:71); TASQ (SEQ ID NO:72); TASL (SEQ ID NO:73), SVIS (SEQ ID NO:74); NVIS (SEQ ID NO:75); GGG; TSRD (SEQ ID NO:76); SPMD (SEQ ID NO:77); DLGE (SEQ ID NO:78); or TPTA (SEQ ID NO:79). In another embodiment, the KEX2 site pre-sequence is not any of the KEX2 site pre-sequences disclosed in U.S. Pat. No. 8,198,046, the disclosure of which is hereby incorporated by reference in its entirety.

The engineered KEX2 site pre- and/or post-sequences provided herein result in enhanced cleavage and/or secretion of a polypeptide of interest from a host cell as compared to the cleavage and/or secretion of the polypeptide of interest from an equivalent fusion polypeptide lacking the KEX2 site pre- and/or post-sequences provided herein.

The KEX2 site pre- and/or post-sequences provided herein can be an optimized KEX2 site pre- and/or post-sequence. An optimized KEX2 pre- and/or post-sequence is a KEX2 pre- and/or post-sequence described by the instant disclosure but which provides greater or more efficient cleavage or secretion (i.e. greater than about 90%, 91%, 92%, 93%, 94%, 95%, 96%, 97%, 98%, 99%, or 100% cleavage or secretion relative to unmodified sequences) from a host cell as compared to other variant KEX2 site pre- and/or post-sequences. Any of the fusion polypeptides disclosed herein can include an optimized KEX2 pre- and/or post-sequence as the KEX2 pre- and/or post-sequence. The optimized KEX2 pre- and/or post-sequence can be employed with any signal sequence, any carrier region from a secreted protein, any KEX2 site, or any polypeptide of interest. A KEX2 region containing an optimized KEX2 site pre- and/or post-sequence can be non-naturally occurring. In certain embodiments, a KEX2 region containing an optimized KEX2 site pre- and/or post-sequence is not found in any protein that is secreted from a host cell, such as, but not limited to, a filamentous fungal host cell.

4. Polypeptides of Interest

The polypeptide of interest in the fusion polypeptide can be any portion of a protein that can be secreted from a host cell (such as a eukaryotic host cell, for example, a mammalian or filamentous fungal host cell), which proteins include, so called industrial enzymes, therapeutic proteins, hormones, structural proteins, plasma proteins, food additives and foodstuffs and the like. The polypeptide of interest can be a heterologous or homologous protein and can include hybrid polypeptides that comprise a combination of partial or complete polypeptides each of which can be homologous or heterologous with respect to the expression host. The secreted polypeptide of interest can be derived from bacterial (e.g. *Bacillus* species and *Pseudomonas* species) fungal (e.g. *Aspergillus, Trichoderma, Humicola*, or *Mucor* species), viral (e.g. Hepatitis A or B or Adenovirus), mammalian (e.g. human, rat, or mouse), or plant sources. Polypeptides of interest can additionally include naturally occurring allelic variations of proteins as well as engineered variations. In additional embodiments, the polypeptide of interest can be a heterotetramer, such as an antibody. In further embodiments, the polypeptides of the heterotetramer can result from one or more fusion polypeptide cleavage events.

In one embodiment, the polypeptide of interest can be an enzyme such as a carbohydrase, such as a starch hydrolyzing α-amylase, an alkaline α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a granular starch hydrolyzing enzyme, such as a glucoamylase or an alpha amylase; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; a phenol oxidizing enzyme, e.g., a laccase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, a aspartic β-decarboxylase, a fumarese or a histadase; a transferase such as cyclodextrin glycosyltranferase or an acyl transferase; or a ligase, for example. In particular embodiments, the protein can be an aminopeptidase, a carboxypeptidase, a chitinase, a glucoamylase, an alpha amylase, a cutinase, a phytase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase.

In other embodiments, the polypeptide of interest can be a therapeutic protein (i.e., a protein having a therapeutic biological activity). Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, immunoglobulin, such as immunoglobulin G (IgG), IgG fragments, IgG fusions, IgM or IgA; interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist.

In some embodiments, the polypeptide of interest is an immunoglobulin (i.e., an antibody) from any class, G, A, M, E or D. (See, U.S. Pat. No. 4,816,567, incorporated herein by reference and references cited therein for a discussion of immunoglobulin structure). In other embodiments, the antibody proteins are monoclonal antibodies including heavy or light chains and functional fragments thereof. In further embodiments, humanized antibodies are polypeptides of interest (e.g. trastuzumab (Herceptin®)). In some embodiments, the antibody or functional fragment thereof is an anti-Respiratory Syncytial Virus (RSV) antibody, an anti-ebola virus antibody, an anti-aggregated β-amyloid (Aβ) antibody, an anti-human immunodeficiency virus (HIV) antibody, an anti-herpes simplex virus (HSV) antibody, an anti-sperm antibody (such as an anti-human contraceptive antigen (HCA) antibody), and anti-HER2/neu antibody. Some specific examples of monoclonal antibody fragments are truncated forms of the heavy chain to remove part of the constant region such as Fab fragments in which the heavy chain (Fd) lacks the hinge region and the CH2 and CH3 domains; Fab' fragments in which the heavy chain includes the hinge region but lacks the CH2 and CH3 domains; and F(ab')2 fragments which includes the Fab portion connected by the hinge region. (Verma et al., (1998) J. Immunological Methods 216:165-181 and Pennell and Eldin (1998) Res. Immunol. 149:599-603, incorporated by reference herein). Also of interest are single chain antibodies (ScFv) and single domain antibodies (e.g., camelid antibodies), and fusion proteins in which a protein is stably fused to part of an antibody (e.g., Fc-fusion proteins). In some embodiments, the antibody is engineered to improve one or more properties (e.g., stability, manufacturability, and/or binding to an antigen).

In some embodiments, a fusion polypeptide will comprise, in operable linkage, a signal sequence; a carrier protein; a KEX2 region and a polypeptide of interest.

B. Polynucleotides

Another aspect of the compositions and methods disclosed herein is a polynucleotide or a nucleic acid sequence that encodes a fusion polypeptide, such as any of the engineered KEX2-region containing fusion polypeptides disclosed herein.

A fusion DNA construct encoding a fusion polypeptide as disclosed above is provided herein, comprising in operable linkage a promoter; a first DNA molecule encoding a signal sequence; a second DNA molecule encoding a carrier protein; a third DNA molecule encoding a KEX2 region, said KEX2 region comprising a KEX2 site and a KEX2 site pre-sequence immediately 5' to the KEX2 site and a KEX2 site post-sequence immediately 3' to the KEX2 site; and a fourth DNA molecule encoding a polypeptide of interest. The components of the fusion DNA construct can occur in any order. Since the genetic code is known, the design and production of these nucleic acids is well within the skill of an ordinarily skilled artisan, given the description of the fusion polypeptide disclosed herein. In certain embodiments, the nucleic acids can be codon optimized for expression of the fusion polypeptide in a particular host cell. Since codon usage tables are available for many species of, for example, mammalian cells and filamentous fungi, the design and production of codon-optimized nucleic acids that encodes a subject fusion polypeptide would be well within the skill of one of skill in the art.

C. Promoters

Examples of suitable promoters for directing the transcription of a nucleic acid in a host cell (for example, a filamentous fungal host cell) are promoters obtained from the genes for Aspergillus oryzae TAKA amylase, Rhizomucor miehei aspartic proteinase, Aspergillus niger neutral alpha-amylase, Aspergillus niger acid stable alpha-amylase (Korman et al (1990) Curr. Genet 17:203-212; Gines et al., (1989) Gene 79: 107-117), Aspergillus niger or Aspergillus awamori glucoamylase (glaA) (Nunberg et al., (1984) Mol. Cell Biol. 4:2306-2315; Boel E. et al., (1984) EMBO J. 3: 1581-1585), Rhizomucor miehei lipase, Aspergillus oryzae alkaline protease, Aspergillus oryzae triose phosphate isomerase, Aspergillus nidulans acetamidase (Hyner et al., (1983) Mol. Cell. Biol. 3:1430-1439), Fusarium venenatum amyloglucosidase, Fusarium oxysporum trypsin-like protease (WO 96/00787), Trichoderma reesei cellobiohydrolase I (Shoemaker et al. (1984) EPA EPO 0137280), Trichoderma reesei cellobiohydrolase II, Trichoderma reesei endoglucanase I, Trichoderma reesei endoglucanase II, Trichoderma reesei endoglucanase III, Trichoderma reesei endoglucanase IV, Trichoderma reesei endoglucanase V, Trichoderma reesei xylanase I, Trichoderma reesei xylanase II, Trichoderma reesei beta-xylosidase, as well as the NA2-tpi promoter (a hybrid of the promoters from the genes for Aspergillus niger neutral alpha-amylase and Aspergillus oryzae triose phosphate isomerase); and mutant, truncated, and hybrid promoters thereof. Reference is also made to Yelton et al., (1984) Proc. Natl. Acad. Sci. USA 81:1470-1474; Mullaney et al., (1985) Mol. Gen. Genet. 199:37-45; Lockington et al., (1986) Gene 33: 137-149; Macknight et al., (1986) Cell 46: 143-147; Hynes et al., (1983) Mol. Cell Biol. 3: 1430-1439. Higher eukaryotic promoters such as SV40 early promoter (Barclay et al (1983) Molecular and Cellular Biology 3:2117-2130) can also be useful. Promoters can be constitutive or inducible promoters. Exemplary promoters include a Trichoderma reesei cellobiohydrolase I or II, a Trichoderma reesei endoglucanase I, II or III, and a Trichoderma reesei xylanase II.

D. Vectors

A polynucleotide encoding any of the fusion polypeptides disclosed herein can be present in a vector, for example, a phage, plasmid, viral, or retroviral vector. In certain embodiments, the vector can be an expression vector for expressing a subject fusion polypeptide in a filamentous fungal cell.

Vectors for expression of recombinant proteins are well known in the art (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.).

A fusion DNA construct can be constructed using well known techniques as is generally described for example in European Patent Application Publication No. 0 215 594, the disclosure of which is incorporated by reference herein.

Natural or synthetic polynucleotide fragments encoding for the polypeptide of interest (e.g. an immunoglobulin) can be incorporated into heterologous nucleic acid constructs or vectors, capable of introduction into and replication in a host cell (e.g., a filamentous fungal host cell).

Once a DNA construct or more specifically a fusion DNA construct is made it can be incorporated into any number of vectors as is known in the art. While the DNA construct will in some embodiments include a promoter sequence, in other embodiments the vector will include other regulatory sequences functional in the host to be transformed, such as ribosomal binding sites, transcription start and stop sequences, terminator sequences, polyadenylation signals, enhancers and or activators. In some embodiments, a polynucleotide encoding the polypeptide of interest and KEX2 region will be inserted into a vector which comprises a promoter, signal sequence and carrier protein at an appropriate restriction endonuclease site by standard procedures. Such procedures and related sub-cloning procedures are deemed to be within the scope of knowledge of those skilled in the art.

Terminator sequences which are recognized by the expression host to terminate transcription can be operably linked to the 3' end of the fusion DNA construct encoding the fusion protein to be expressed. Those of general skill in the art are well aware of various terminator sequences that can be used with host cells, such as, filamentous fungi. Non-limiting examples include the terminator from the *Aspergillus nidulans* trpC gene (Yelton M. et al., (1984) *Proc. Natl. Acad. Sci. USA* 81: 1470-1474) or the terminator from the *Aspergillus niger* glucoamylase genes (Nunberg et al. (1984) *Mol. Cell. Biol.* 4: 2306-2353) or the terminator from the *Trichoderma reesei* cellobiohydrolase I gene.

Polyadenylation sequences are DNA sequences which when transcribed are recognized by the expression host to add polyadenosine residues to transcribed mRNA. Examples include polyadenylation sequences from *A. nidulans* trpC gene (Yelton et al (1984) *Proc. Natl. Acad Sci. USA* 81; 1470-1474); from *A. niger* glucoamylase gene (Nunberg et al. (1984) *Mol. Cell. Biol.* 4:2306-2315); the *A. oryzae* or *A. niger* alpha amylase gene and the *Rhizomucor miehei* carboxyl protease gene.

In further embodiments, the fusion DNA construct or the vector comprising the fusion DNA construct will contain a selectable marker gene to allow the selection of transformed host cells. Selection marker genes are well known in the art and will vary with the host cell used. Examples of selectable markers include but are not limited to ones that confer antimicrobial resistance (e.g. hygromycin, bleomycin, chloroamphenicol and phleomycin). Genes that confer metabolic advantage, such as nutritional selective markers can also find use. Some of these markers include amdS. Also, sequences encoding genes which complement an auxotrophic defect can be used as selection markers (e.g. pyr4 complementation of a pyr4 deficient *A. nidulans*, *A. awamori* or *Trichoderma reesei* and argB complementation of an argB deficient strain). Reference is made to Kelley et al., (1985) *EMBO J.* 4: 475-479; Penttila et al., (1987) *Gene* 61:155-164 and Kinghorn et al (1992) Applied Molecular Genetics of Filamentous Fungi, Blackie Academic and Professional, Chapman and Hall, London, the disclosure of each of which are incorporated by reference herein.

E. Host Cells

The expression cassette or vector can be introduced into a suitable expression host cell, which then expresses the corresponding polynucleotide encoding a fusion polypeptide Suitable host cells include cells of any microorganism (e.g., cells of a bacterium, a protist, an alga, a fungus (e.g., a yeast or filamentous fungus), or other microbe), and can be cells of a bacterium, a yeast, or a filamentous fungus. Fungal expression hosts can be, for example, yeasts, which can also serve as ethanologens. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable for producing the polypeptide.

Suitable host cells of the bacterial genera include, but are not limited to, cells of *Escherichia*, *Proteus*, *Bacillus*, *Ralstonia*, *Lactobacillus*, *Lactococcus*, *Pseudomonas*, *Staphylococcus*, and *Streptomyces*. Suitable cells of bacterial species include, but are not limited to, cells of *Escherichia coli*, *Bacillus subtilis*, *Bacillus licheniformis*, *Bacillus megaterium*, *Lactobacillus brevis*, *Pseudomonas aeruginosa*, *Pseudomonas fluorescens*, *Pseudomonas stutzerei*, *Staphylococcus carnosus*, *Lactococcus lactis*, *Ralstonia eutropha*, *Proteus mirabilis*, and *Streptomyces lividans*.

Suitable host cells of the genera of yeast include, but are not limited to, cells of *Saccharomyces*, *Schizosaccharomyces*, *Candida*, *Hansenula*, *Pichia*, *Kluyveromyces*, *Yarrowia* and *Phaffia*. Suitable cells of yeast species include, but are not limited to, cells of *Saccharomyces cerevisiae*, *Schizosaccharomyces pombe*, *Candida albicans*, *Hansenula polymorpha*, *Yarrowia lipolytica*, *Pichia pastoris*, *P. canadensis*, *Kluyveromyces marxianus*, and *Phaffia rhodozyma*.

Suitable host cells of filamentous fungi include all filamentous forms of the subdivision Eumycotina. Suitable cells of filamentous fungal genera include, but are not limited to, cells of *Acremonium*, *Aspergillus*, *Aureobasidium*, *Bjerkandera*, *Ceriporiopsis*, *Chrysoporium*, *Coprinus*, *Coriolus*, *Corynascus*, *Chaertomium*, *Cryptococcus*, *Filobasidium*, *Fusarium*, *Gibberella*, *Humicola*, *Magnaporthe*, *Mucor*, *Myceliophthora*, *Mucor*, *Neocallimastix*, *Neurospora*, *Paecilomyces*, *Penicillium*, *Phanerochaete*, *Phlebia*, *Piromyces*, *Pleurotus*, *Scytaldium*, *Schizophyllum*, *Sporotrichum*, *Talaromyces*, *Thermoascus*, *Thielavia*, *Tolypocladium*, *Trametes*, and *Trichoderma*.

Suitable cells of filamentous fungal species include, but are not limited to, cells of *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium lucknowense*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Neurospora intermedia*, *Penicillium purpurogenum*, *Penicillium canescens*, *Penicillium solitum*, *Penicillium funiculosum* *Phanerochaete chrysosporium*, *Phlebia radiate*, *Pleurotus eryngii*, *Talaromyces flavus*, *Thielavia terrestris*, *Trametes villosa*, *Trametes versicolor*, *Trichoderma harzianum*, *Trichoderma koningii*, *Trichoderma longibrachiatum*, *Trichoderma reesei*, and *Trichoderma viride*.

Promoters and/or signal sequences associated with secreted proteins in a particular host of interest are candidates for use in the heterologous production and secretion of fusion polypeptides in that host or in other hosts. As a non-limiting example, in filamentous fungal systems, the promoters that drive the genes for cellobiohydrolase I (cbh1), glucoamylase A (glaA), TAKA-amylase (amyA), xylanase (ex1A), the gpd-promoter cbh1, cbhll, endoglucanase genes eg1-eg5, Cel61B, Cel74A, gpd promoter, Pgk1, pki1, EF-1alpha, tef1, cDNA1 and hex1 are suitable and can be derived from a number of different organisms (e.g., *A. niger*, *T. reesei*, *A. oryzae*, *A. awamori*, *A. nidulans*).

In some embodiments, the polynucleotide encoding a fusion polypeptide is recombinantly associated with a polynucleotide encoding a suitable homologous or heterologous signal sequence that leads to secretion of the recombinant polypeptide into the extracellular (or periplasmic) space, thereby allowing direct detection of enzyme activity in the cell supernatant (or periplasmic space or lysate). Suitable signal sequences for *Escherichia coli*, other gram-negative bacteria and other organisms known in the art include those that drive expression of the HlyA, DsbA, Pbp, PhoA, PelB, OmpA, OmpT or M13 phage Gill genes. For *Bacillus subtilis*, Gram-positive organisms and other organisms known in the art, suitable signal sequences further include those that drive expression of the AprE, NprB, Mpr, AmyA, AmyE, Blac, SacB, and for *S. cerevisiae* or other yeast, including the killer toxin, Bar1, Suc2, Mating factor alpha, Inu1A or Ggplp signal sequence. Signal sequences can be cleaved by a number of signal peptidases, thus removing them from the rest of the expressed protein.

In some embodiments, the fusion polypeptide is expressed alone or as a fusion with additional peptides, tags or proteins located at the N- or C-terminus (e.g., 6×His, HA or FLAG tags). Suitable fusions include tags, peptides or proteins that facilitate affinity purification or detection (e.g., 6×His, HA, chitin binding protein, thioredoxin or FLAG tags), as well as those that facilitate expression, secretion or processing of the target beta-glucosidases. In addition to KEX2, further suitable processing sites include enterokinase, STE13, or other protease cleavage sites known in the art for cleavage in vivo or in vitro.

Polynucleotides encoding fusion polypeptides can be introduced into expression host cells by a number of transformation methods including, but not limited to, electroporation, lipid-assisted transformation or transfection ("lipofection"), chemically mediated transfection (e.g., CaCl and/ or CaP), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

III. Methods

A. Fusion Polypeptide Production

Additionally provided herein are methods for producing one or more of the fusion polypeptides disclosed herein in a host cell (such as, without limitation, a mammalian or filamentous fungal host cell). In some embodiments these methods include, obtaining a host cell comprising a fusion DNA construct or vector disclosed herein and culturing the host cell under suitable conditions which allow the expression and secretion of the polypeptide of interest. While a culture of host cells (i.e., a composition containing host cells and growth media) can contain the secreted protein of the fusion polypeptide described herein, in some embodiments the polypeptide of interest is recovered from the culture media. In other embodiments, the polypeptide of interest is purified. Protein can be recovered and/or purified from growth media by any convenient method known in the art.

In some embodiments, a subject host cell (such as, a fungal host cell) can be cultured under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which can also find use. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are known.

B. Expression and Secretion

The production of a polypeptide of interest in a host cell (e.g., a filamentous fungal host cell) comprising a fusion DNA construct encoding a fusion polypeptide results in the secretion of the polypeptide of interest of the fusion polypeptide. During the secretion process in, for example, fungi, sugar chains may be attached to a protein to be secreted to produce a glycosylated protein. Accordingly, in some embodiments, the production of the polypeptide of interest, (e.g. an antibody), may include glycosylated or non-glycosylated protein.

In some embodiments, the secreted protein of the subject fusion polypeptide is generally present in the culture medium of the host cell at an amount that is higher than the amount of the secreted polypeptide of interest of an equivalent fusion polypeptide that lacks the engineered KEX2 site pre- and/or post-sequences disclosed herein, produced by an equivalent host cell (i.e., the same cell type, grown under the same conditions). A culture of the subject cells producing a polypeptide of interest from a fusion polypeptide in accordance with the methods disclosed herein can contain more than about 5%, more than about 10%, more than about 20%, more than about 40%, more than about 60%, more than about 80%, more than about 100%, more than about 150%, more than about 200%, more than about 300%, more than about 500%, or more than about 1000% polypeptide of interest in the growth medium, as compared to an equivalent cell culture that expresses an otherwise equivalent protein that does not have the engineered KEX2 site pre- and/or post-sequences as encompassed by the present disclosure.

In some embodiments, the level of expression and secretion for a polypeptide of interest (e.g. a full-length antibody) will be greater than 0.5 g/L. Routinely greater than 1.0 g/L of the polypeptide of interest may be recovered from a culture media. Reproducible levels of greater than about 1.5, 2.0, 3.0, 4.0, 5.0, 6.0, 7.0, 8.0, 9.0, 10, 1, 112, 13, 14, 15, 16, 17, 18, 19, 20, 21, 22, 23, 24, or 25 g/L may be attained. In some embodiments, the level of expression and secretion of the polypeptide of interest will be greater than about 30 g/L and even greater than about 40 g/L.

In other embodiments, the ratio of the secreted cleaved polypeptide of interest to the uncleaved secreted polypeptide of interest is greater than about 5:1, 10:1, 15:1, 20:1, 25:1, 30:1, 35:1, 40:1, 50:1, 55:1, 60:1, 65:1, 70:1, 75:1, 80:1, 85:1, 90:1, 95:1, 100:1. 150:1, 200:1, 250:1, 300:1, 350:1, 400:1, 450:1, 500:1, 1000:1, 5000:1, 7500:1, 10000:1, or 100000:1, inclusive of all values falling in between these ratios.

In some embodiments, the cleavage of the polypeptide of interest from the recombinant fusion polypeptide will be greater than the cleavage of the same polypeptide of interest from an equivalent recombinant fusion polypeptide which lacks the KEX2 site pre- and/or post-sequences disclosed herein. In some embodiments, the KEX2 site pre- and/or post-sequence may result in a fusion protein that is cleaved to at least about 80%, at least about 85%, at least about 90%, at least about 91%, at least about 92%, at least about 93%, at least about 94%, at least about 95%, at least about 96%, at least about 97%, at least about 98%, at least about 99% or at least about 100% efficiency, wherein 100% efficiency results in a completely cleaved polypeptide of interest from the fusion polypeptide.

In certain embodiments, the efficiency of protein cleavage may be calculated by determining amount of cleavage that has occurred, e.g., by determining the amount of cleaved versus the amount of uncleaved protein. In one embodiment, the amount of protein cleavage may be calculated by determining the ratio of the amount of cleaved protein in the growth medium to the amount of non-cleaved fusion protein in the growth medium per volume of cell culture.

A fusion polypeptide containing a KEX2 site pre- and/or post-sequence or an optimized KEX2 site pre- and/or post-sequence can, in certain embodiments, result in a fusion polypeptide that is cleaved to at least about 30%, 40%, 50%, 60%, 70%, 80%, 90%, 91%, 92%, 93%, 94%, 95%, 96%, 97%, 98%, 99% or 100% efficiency, wherein 100% efficiency is a completely cleaved polypeptide of interest.

In other embodiments, the efficiency of secretion of a subject fusion polypeptide may be calculated by determining the amount of the secreted portion of that fusion polypeptide in the growth medium of a cell secreting that protein. This determination may be quantitative, qualitative, relative or absolute. In one embodiment, the amount of secreted protein in the growth medium of a cell secreting a subject fusion may be at least about 10%, at least about 30%, at least about 50%, at least about 70%, at least about 90%, at least twice, at least five times, or at least ten times greater than the amount of the secreted protein secreted by a cell producing an equivalent fusion polypeptide that does not contain an optimized KEX2 pre- and/or post-sequence.

In some embodiments, the increase in secretion and/or cleavage may be measured against a standard KEX2 region defined as GGGB1B2, wherein B1B2 is KK, KR, RK or RR and preferably KR. In an embodiment, the amount of secreted protein or polypeptide of interest in the growth medium of a cell secreting a subject fusion may be at least about 10%, at least about 30%, at least about 50%, at least about 70%, at least about 80%, at least about 90%, at least about 100%, at least 2×, at least 3×, at least 5×, and at least 10× greater than the amount of the secreted protein or polypeptide of interest secreted by an equivalent fusion polypeptide in an equivalent host under essentially the same conditions.

IV. Kits

Further provided herein are kits containing one or more of written instructions for producing any of the fusion polypeptides disclosed herein; one or more of any of the nucleic acids disclosed herein; any of the vectors disclosed herein; any of the host cells disclosed herein. The kits can further include one or more of a composition comprising a Kex2 serine peptidase and/or a nucleic acid encoding a Kex2 serine peptidase. Additionally, the kits can also include a host cell that expresses a Kex2 serine peptidase, one or more compositions comprising an additional protease; and/or nucleic acids encoding one or more additional protease.

The invention can be further understood by reference to the following examples, which are provided by way of illustration and are not meant to be limiting.

EXAMPLES

Example 1: Assays

In the following examples, various assays were used as set forth below for ease in reading. Any deviations from the protocols provided below are indicated in the relevant sections. In these experiments, a spectrophotometer was used to measure the absorbance of the products formed after the completion of the reactions.

Figure 2:
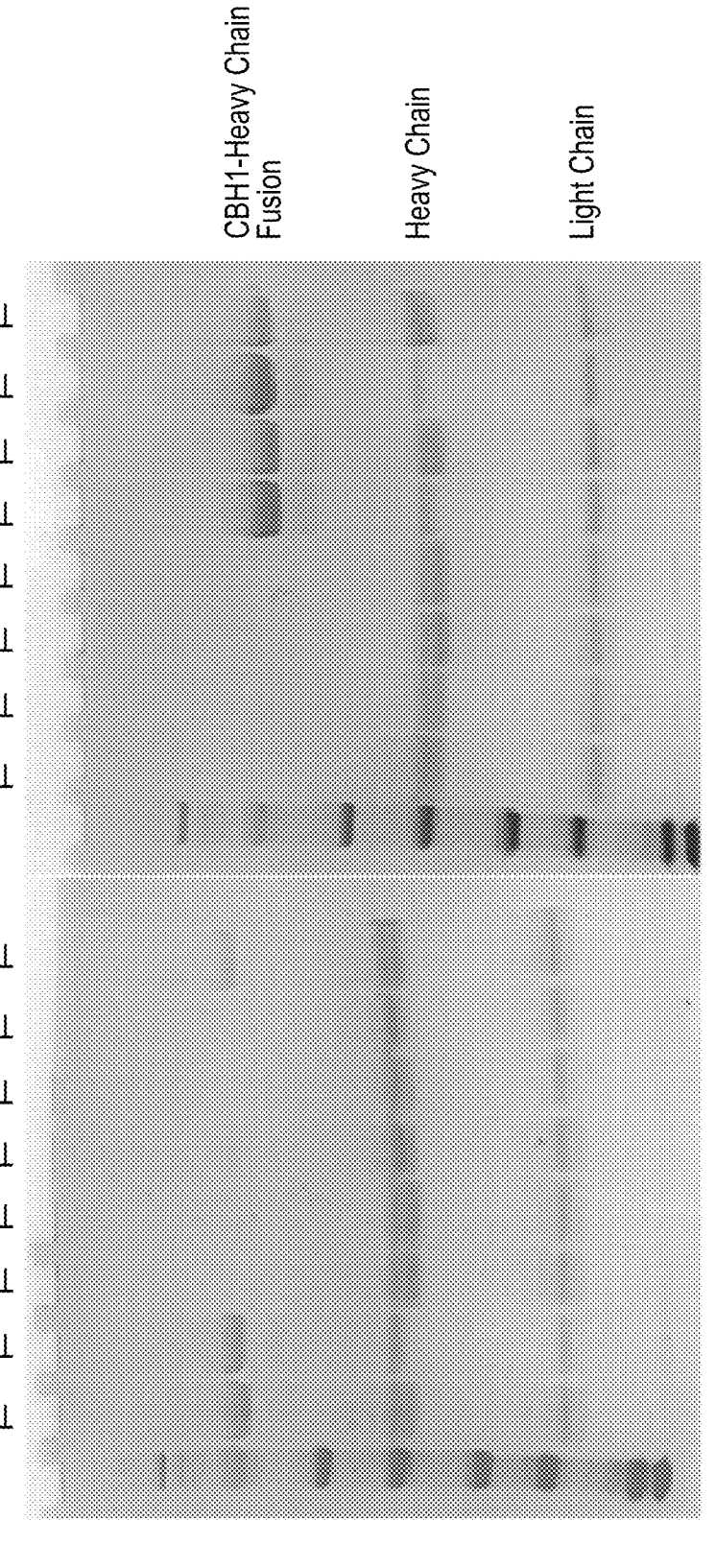
FIG. 2 depicts a representative SDS-PAGE gel showing cleavage efficiency of selected engineered KEX2 recognition sequences. Unaltered sequence indicated by asterisk (*).

Protein Secretion Assay: This method measures the amount of a secreted protein (polypeptide of interest) released or cleaved from a fusion polypeptide in a growth medium relative to the amount of the secreted protein that remains in the form of the fusion polypeptide (e.g. attached to the carrier protein). Fusion polypeptide and polypeptide of interest were purified from the crude broth from *T. reesei* using protein A resin. A 96 well plate with protein A resin was first equilibrated in PBS, the pH of the culture broth was adjusted to pH7 using 1M sodium phosphate, then the broth was filtered and the filtrate was incubated with the resin in 96 well plate for 5 mins with shaking. PBS was used to wash off any proteins that did not bind to protein A resin, the bound proteins were eluted from resin using 100 mM Glycine pH2.7, followed by neutralization with 1M Tris pH9. The purified protein of each variant was run on SDS-PAGE gel (FIG. 2). Based on the molecular weight of fusion polypeptide and polypeptide of interest, the band intensity of these proteins can be quantitated using image quant software. The ratio of fusion polypeptide to polypeptide of interest can be calculated.

CBH1 hydrolysis: For comparing the ratio of fusion polypeptide to polypeptide of interest of different variants, carrier protein CBH1 in the fusion polypeptide was quantitated by measuring CBH1 hydrolysis on its substrate 4-Nitrophenyl β-D-lactopyranoside (pNP, Sigma). 10 µl of the purified protein was incubated with 40 µl of 2.5 mM pNPL in 50 mM sodium acetate buffer pH5 in 384 well plates. The plate was sealed and incubated at 50° C. for one hour at 1400 rpm shaking. After one hour incubation, 200 of 500 mM sodium carbonate buffer pH10 was added into each well in a 384 well Greiner plate to stop the reaction. The OD405 was measured to quantitate relative CBH1 concentration in polypeptide. The total polypeptide and polypeptide of interest concentration was measured using protein A probe on Octet system (ForteBio). CBH1 activity was normalized to total polypeptide and polypeptide of interest concentration. Performance indices (PI) was calculated for each variant by dividing normalized CBH1 activity of unaltered control to variant's normalized CBH1 activity. Variants with PIs of 8 or higher indicates more than >90% cleavage of CBH1 from fusion polypeptide. Variants without any CBH1 activity indicate the complete cleavage of CBH1 from fusion polypeptide.

Example 2: Generation and Evaluation of Site Evaluation Libraries

A. Plasmids and Site Evaluation Construction for Anti-RSV HC Heavy Chain

Sequences for the heavy chain of monoclonal antibodies against respiratory syncytial virus (palivizumab or Synagis) were codon optimized and synthesized by GeneArt GmH (Germany). To prevent from potential degradation by Kex2 furin-like protease during expression in a fungal cell, a lysine at position 251 in the heavy chain was mutated to threonine (K251T). Initially synthetic sequences of the anti-RSV HC were cloned individually behind a catalytical core of the *Trichoderma reesei* native cellobiohydrolase I (CBH1) together with its linker region (1-479 aa). To release mature antibody chains from the carrier partner a Kex2 cleavage site was introduced between the linker and HC.

Figure 3:
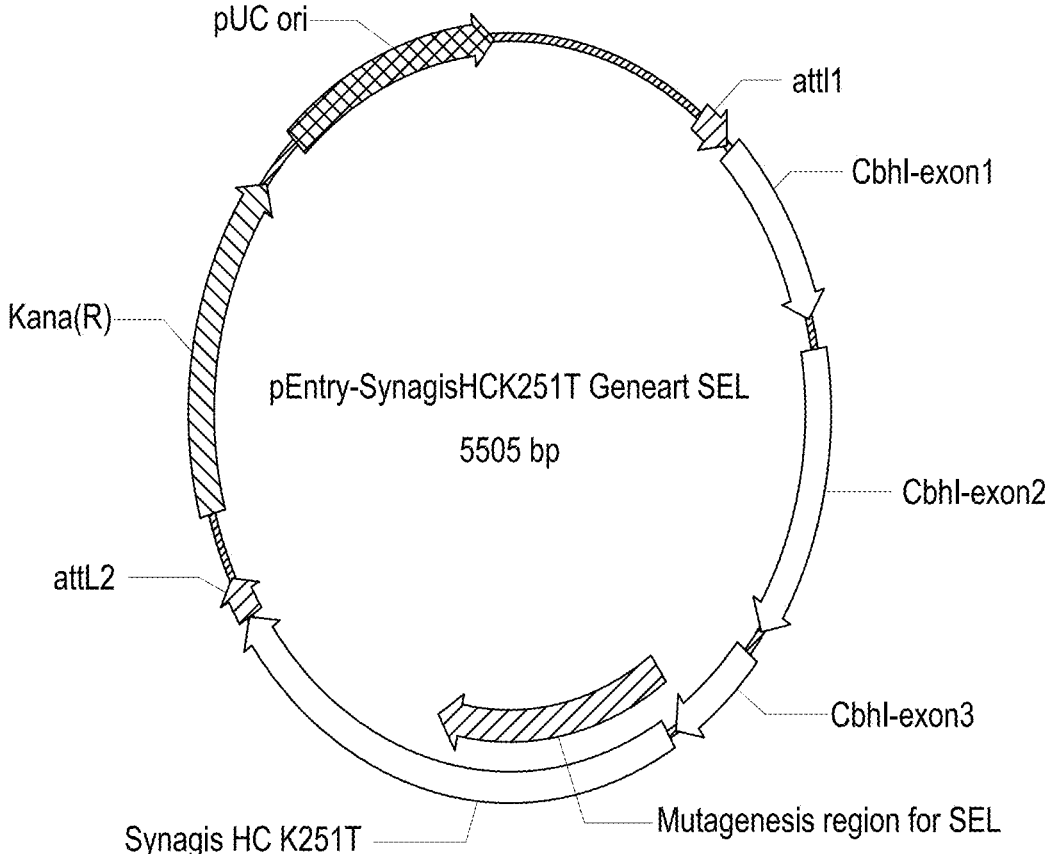
FIG. 3 depicts a schematic of the entry clone used for Synagis HC heavy chain SEL library construction.

A fusion construct of cbhI-HC_Synagis was then amplified by PCR with gene specific primers extended with the attB1 and attB2 sites to allow for the Gateway® BP recombination cloning into pDonor221 vector (Invitrogen, USA). Plasmid pEntry-SynagisHCK251T_Geneart_SEL, as shown in FIG. 3, was used by the vendor BaseClear (Netherlands) as a template for construction of site evaluation (SEL) library at positions 466-725 an (counting from the CbhI Met). An average number of mutant variants per an position was around 17. Mutated sequences were further cloned via the Gateway® LR recombination technique into pTTTpyr2-ISceI destination vector resulting in the final expression plasmids pTTTpyr2-ISceI-SynagisHC_Geneart_SEL (FIG. 3).

Figure 4:
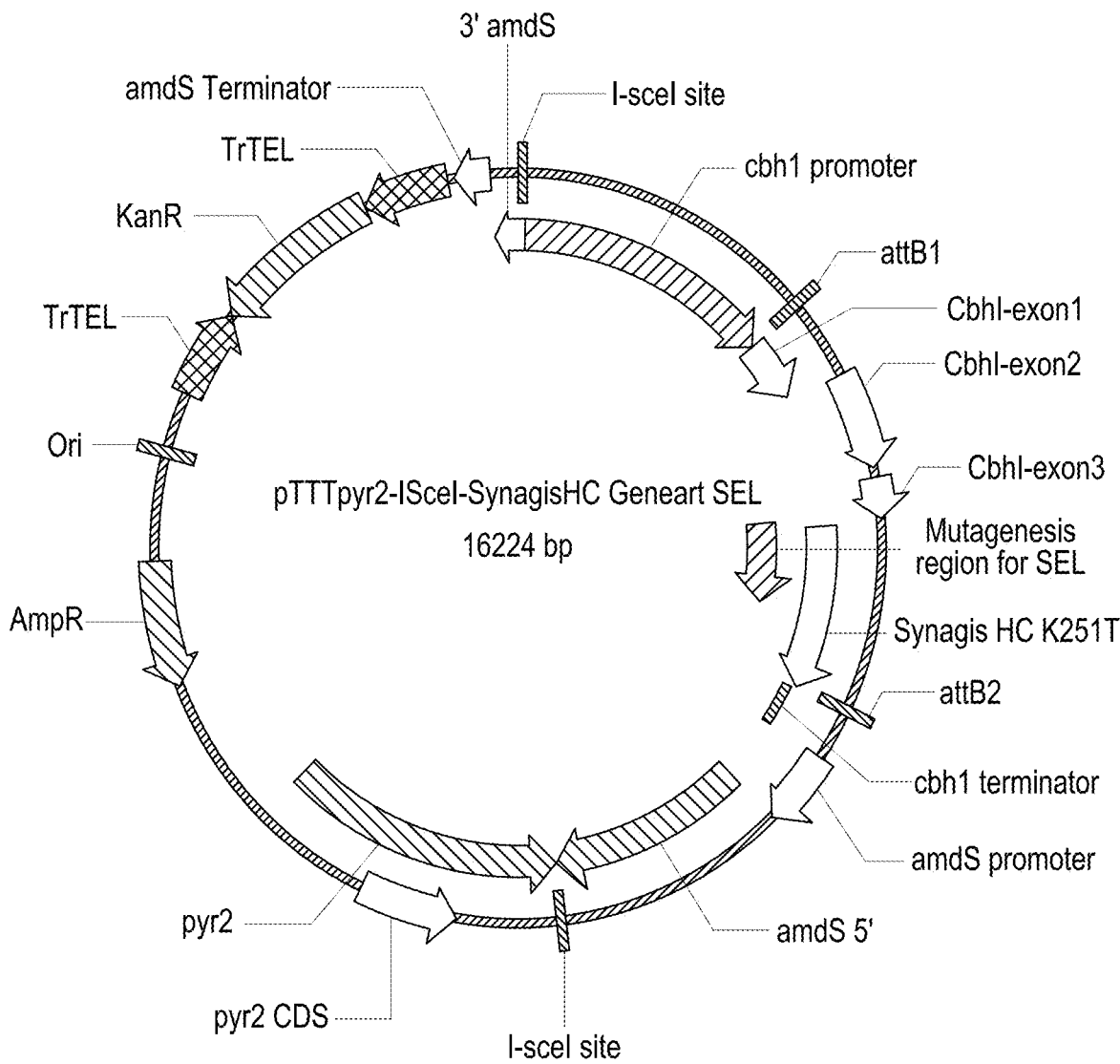
FIG. 4 depicts a schematic of the expression vector pTTTpyr2-ISceI-Synagis HC_Geneart_SEL heavy chain.

This expression vector contains the *T. reesei* cbhI promoter and terminator regions allowing for a strong inducible expression of a gene of interest and the *T. reesei* pyr2 selective marker conferring growth of transformants on minimal medium without supplementation with uridine. The plasmid is maintained autonomously in fungal cells due to *T. reesei* derived telomere regions. Plasmids were propagated in commercially available *Escherichia coli* TOP10 cells (Invitrogen, US), purified, sequence verified, arrayed individually in 96 well MTPs and used for fungal transformation as described below.

pEntry-Synagis_LC_Geneart plasmid was constructed via the Gateway® BP recombination cloning and recombined further with pTrex6g destination vector in a similar way as described above resulting in the expression vector pTrex6g-Synagis_LC. This vector served as a template to generate a PCR fragment expressing the light chain driven by the cbhI promoter and linked to the alS marker conferring resistance to chlorimuron ethyl to a fungal cell (FIG. 4).

B. Fungal Host Strain Construction and Transformation

The expression cassette consists of a CBH1 promoter, CBH1 core, antibody HC and LC connected by CBH1 linker and kex2 for processing of CBH1, CBH1 terminator, and the alS marker conferring resistance to chlorimuron ethyl to a fungal cell. The alS marker was used for making the host strains so that the pyr2 marker was available for the SEL variants. The expression cassette was randomly integrated into the host *T. reesei* genome at multiple copies. The full expression cassette was amplified by PCR. The PCR product was cleaned up and concentrated to 500-1000 ng/µL.

The host *T. reesei* strain used for transformation was deleted for major cellulases and xylanases. The strain was transformed using a standard PEG-protoplast transformation method. Transformation mixtures containing approximately 10 µg of DNA and $5 \times 10^6$ protoplasts in a total volume of 250 µl were treated with 2 mL of 25% PEG solution, diluted with 2 volumes of 1.2M sorbitol/10 mM Tris, pH7.5/10 mM CaCl2 solution, and mixed with 26 mL of 2% low melting agarose containing 1M sorbitol, 1 g/L uridine, 75 mg/L chlorimuron ethyl in minimal medium and distributed over four 10 cm petri plates pre-poured containing 1.5% agarose, 1M sorbitol in minimal media. After sufficient growth transformants from each plate were observed, individual colonies were picked onto fresh 10 cm petri plates containing 1.5% agar, 1 g/L uridine, 75 mg/L chlorimuron ethyl, 4 per plate to allow room for assessing stability. The stable colony phenotype is concentric circular growth with smooth edges. Once stable transformants were observed and well sporulated, spores were harvested and used for inoculation of liquid cultures.

All high throughput transformations with Synagis HC variants were performed robotically in a 24 well MTP format using Biomek robots (Beckman Coulter, USA). Plasmids with variants were received from the vendor in a 96 well format arrayed according to a predetermined layout. Transformation mixtures containing approximately 1 mg of DNA and $5 \times 10^6$ protoplasts in a total volume of 50 ml were treated with 200 µl of 25% PEG solution, diluted with 1 volumes of 1.2M sorbitol/10 mM Tris, pH7.5/10 mM CaCl₂ solution, rearranged robotically into 24 well MTPs and poured in 1 ml of 3% low melting agarose containing 1M sorbitol in minimal medium. After sufficient growth transformants from each well were pooled together and plated on fresh 24 well agar plates with minimal medium. Once sporulated, spores were harvested and used for inoculation of liquid cultures.

C. Fungal Fermentations in Slow Release 24 Well MTPs

To generate sufficiently high antibody titers $10^5$-$10^6$ *T. reesei* spores were inoculated in customer made 24 well MTPs composed of the Sylgard 170 elastomer (from Dow Corning, USA) premixed with lactose which was slowly released in the medium during fermentation to ensure continuous production. Cultures were grown in 1.25 ml of medium containing: 16 g/L glucose, 9 g/L casamino acids, 10 g/L (NH4)2SO4, 4.5 g/L KH2PO4, 1 g/L MgSO4*7H2O, 1 g/L CaCl2*2H2O, 33 g/L PIPPS buffer [pH 5.5], 0.25% *T. reesei* trace elements (100%: 175 g/L citric acid (anhydrous), 200 g/L FeSO4*7H2O, 16 g/L ZnSO4*7H2O, 3.2 g/L CuSO4*5H2O, 1.4 g/L MnSO4*H2O, 0.8 g/L H3BO3).

Plates were incubated in Infors shaker with a 50 mm throw at 200 rpm and 28 C with 80% humidity. After 5-6 days of growth cultures were reformatted back to 96 well deep well MTPs and filtered using 96-well microtiter filter plates (0.2 μm hydrophilic PVDF membrane, Corning, Tewksbury MA). The plates were frozen in Axygen half-deep well plates (P-DW-11-C).

D. Purification

Plates were moved from the freezer to the cold room to allow the samples to gradually thaw overnight at 4° C. Before purification, grown WT samples were removed from the plates and these samples were pooled. One mL per well of pooled WT, pooled low binding control, pooled high binding control, and pooled vector only (vector expressing CBH1 in same strain) samples were added to designated wells. The library plates were grown in duplicate and these controls were added to both plates. The plates gently shook for 2 minutes to homogenize the fluid in the wells followed by centrifugation for 1 minute to pellet any precipitate.

The centrifuged plates were then moved to a robot to remove 20 μL of the crude material for Octet Protein A quantitation. The 20 μL was added to 80 μL of 1×PBS in a 384-well plate (Greiner Bio-One 781209). Four library plates went into one 384-well plate and there was a separate 384-well plate for the duplicate growth of the four plates (plates Xa and Xb).

After samples were removed for the Octet quantitation, the plates were then purified. The robot handled four library plates at a time. The robot added 50 μL of 1 M KPi pH 7 to pH up the supernatant to improve the antibody binding to the Protein A resin. The robot then transferred the crude material (max 880 μL per well) from the four plates to 2 mL filter plates (Pall 8275) filled previously with 220 μL of Protein A resin in PBS. These filter plates then shook for 5 minutes on a shaker. The plates were then filtered by centrifugation at 1000 g for 2 minutes, and the flow through was collected in the empty harvest plate that the samples were transferred from. This material was stored until after quantitation. The filter plates were returned to the robot deck and the duplicate growth plates were added to the same filter plates. These plates were incubated and centrifuged as before. The resin was then washed with 880 μL of PBS buffer. The plates shook for 1 minute and then centrifuged at 1000 g for 2 minutes. The flow through was discarded, and the plates were returned to the robot for the second PBS washing. After the second washing, the plates were moved to a robot running the elution program.

The elution program handled four plates at a time. It added 11 μL of neutralization buffer (1 M Tris pH 9) to a clean half-deep well plate that the samples would be eluted into. The program then added 440 μL of elution buffer (100 mM glycine pH 2.7) to the filter plates. The plates then shook for 1 minute at setting 7 and then were filtered by centrifugation (1000 g for 2 minutes) into the freshly prepped recovery plates. After centrifugation, the sample plates shook for 1 minute to ensure proper mixing of the neutralization buffer.

E. Results

Variants were tested for cleavage efficiency as described in Example 1. A representative SDS-PAGE gel of unaltered and variant KEX2 cleavage sites is shown in FIG. 2. Performance indices (PI) were calculated for each variant with respect to cleavage relative to the unaltered cleavage domain. Variants with PIs of 8 or higher, indicating complete or nearly complete (>90%) cleavage relative to the unaltered amino acid sequence, are indicated in Table 1.

TABLE 1

| Single variant cleavage sites with improved cleavage efficiency | | |
| --- | --- | --- |
| Variant | CBH1 PI | position |
| A482H | 11.6 | A3 |
| A482K | 12.0 | A3 |
| A482R | 29.3 | A3 |
| T479A | 13.4 | T1 |
| T479F | 25.3 | T1 |
| E484F | 9.3 | E5 |
| T479M | 19.5 | T1 |
| T479Q | 17.6 | T1 |
| T479R | 10.2 | T1 |
| T479Y | 22.1 | T1 |
| E484W | 17.5 | E5 |
| Q487D | 32.9 | Q6 |
| Q487G | 21.7 | Q6 |
| S480F | 37.7 | S2 |
| S480H | 22.6 | S2 |
| S480K | 24.6 | S2 |
| S480L | 37.9 | S2 |
| S480M | 28.0 | S2 |
| S480P | 89.0 | S2 |
| S480Q | 14.5 | S2 |
| S480R | 57.1 | S2 |
| S480V | 18.3 | S2 |
| S480W | 10.8 | S2 |
| V488F | 9.8 | V7 |
| V483L | 35.7 | V4 |
| V488L | 21.0 | V7 |

Example 3: Generation and Testing of Combinatorial Variants

Further variants were created that contained multiple substitutions in the linker site from those shown in Table 1 to test the combinability of the substitutions to achieve higher or complete cleavage of the fusion proteins.

The heavy and light chains of the Synagis antibody were assembled onto one vector for co-expression.

Synthetic DNA was cloned into an expression vector for single chain variant transformation into single chain antibody host strains. These vectors had combinations of variants designed based on the SEL data shown in Table 1. A specific subset of variants were chosen to be combined with each other and expressed in host a *T. reesei* strain deleted for major cellulases and xylanases.

Figure 6:
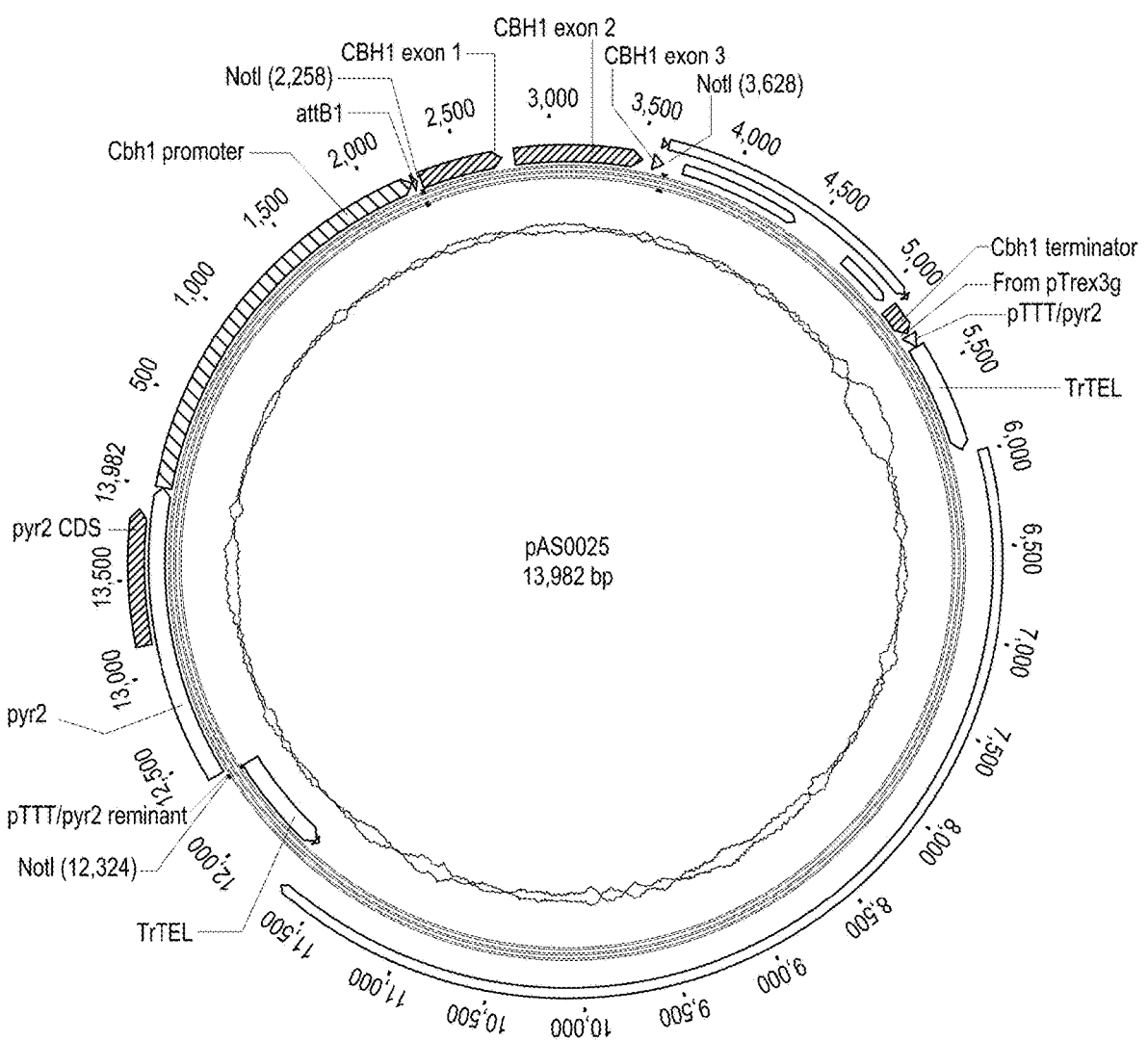
FIG. 6 depicts a schematic of the pAS25 expression vector.
Figure 7A:
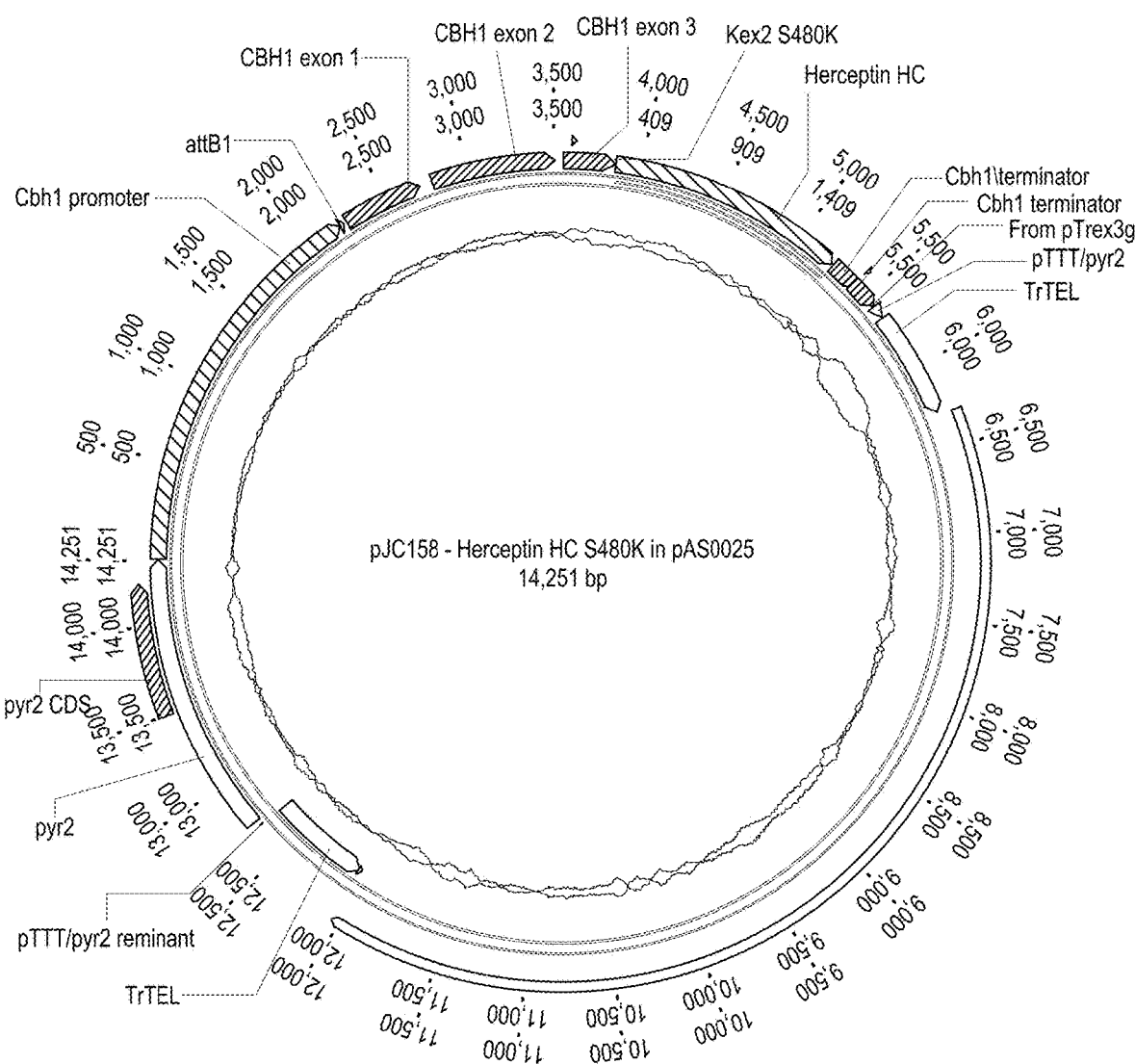
FIG. 7A depicts a schematic of the trastuzumab heavy chain vector with TKVAVEKR kex sequence.
Figure 7B:
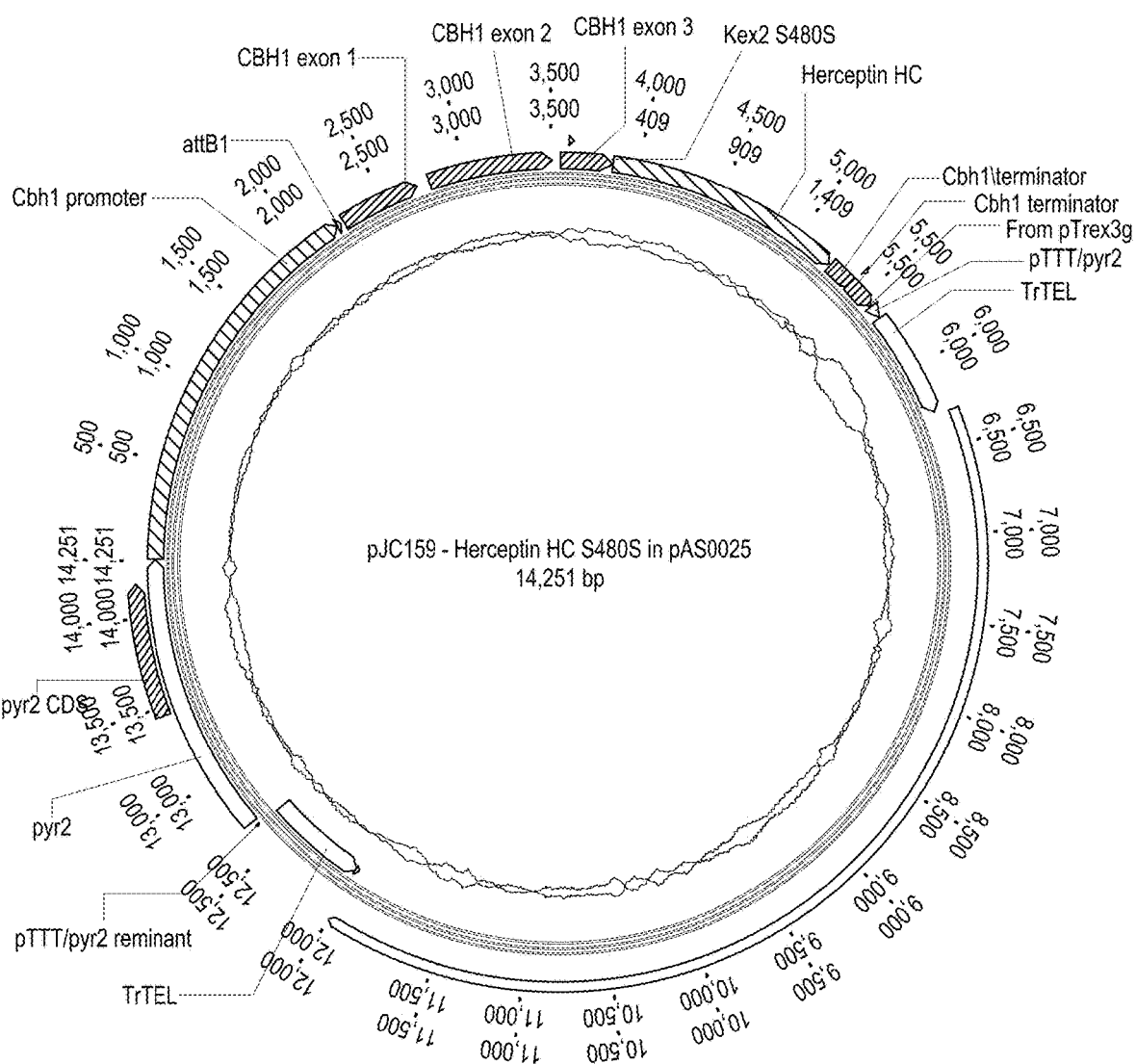
FIG. 7B depicts a schematic of the trastuzumab heavy chain vector with TSVAVEKR kex sequence.
Figure 8A:
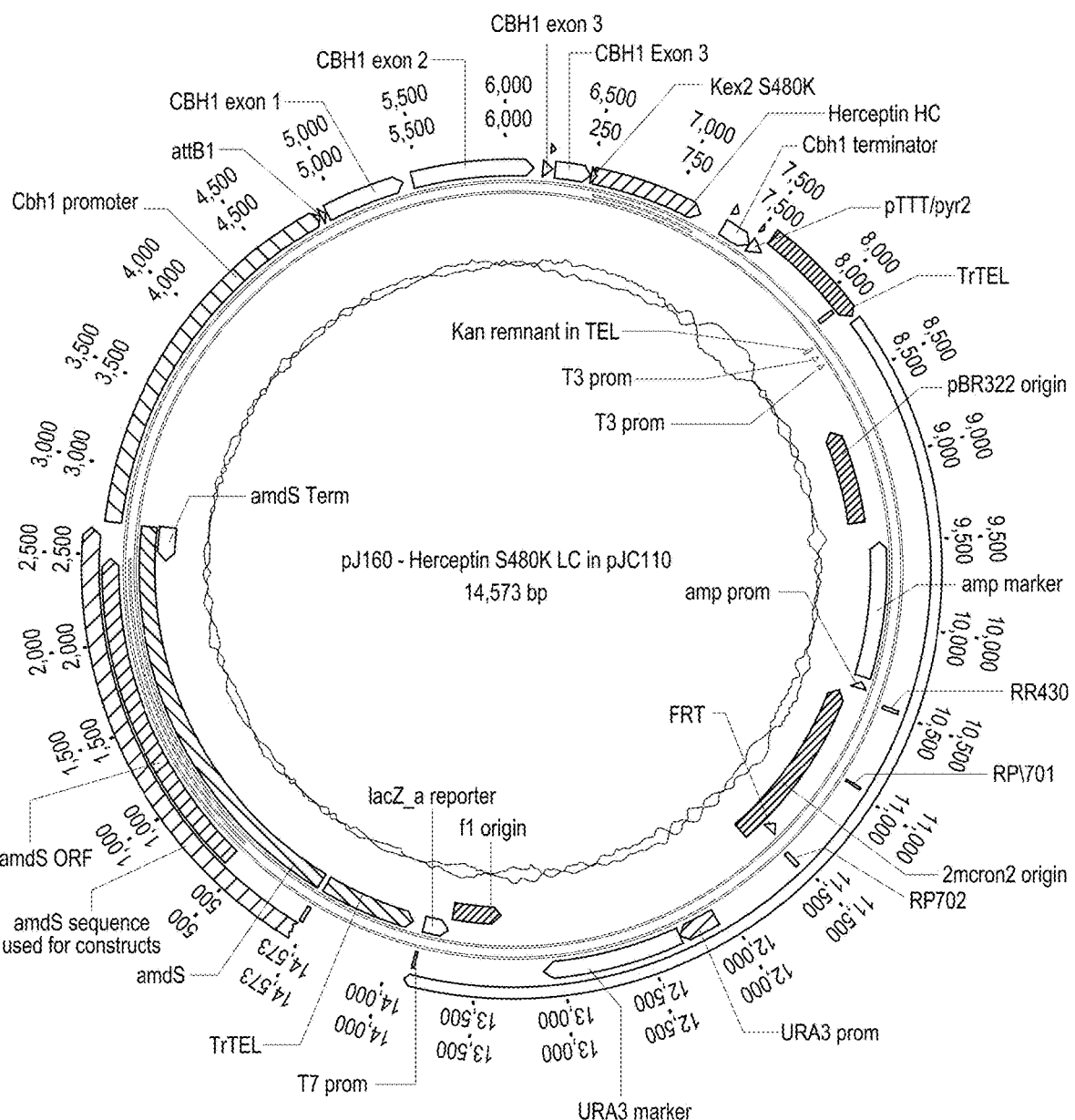
FIG. 8A depicts a schematic of the trastuzumab light chain vector with TKVAVEKR kex sequence.
Figure 8B:
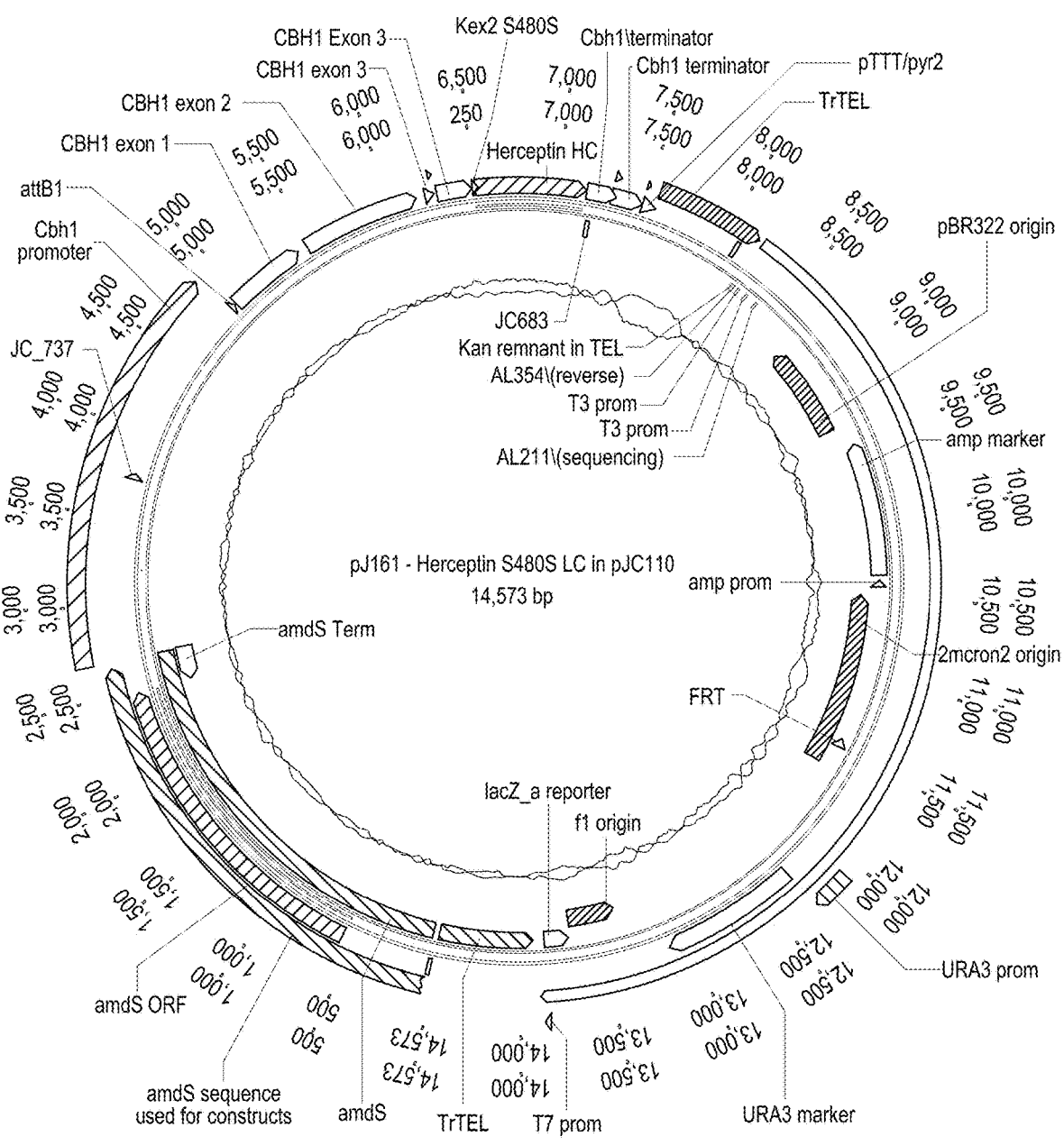
FIG. 8B depicts a schematic of the trastuzumab light chain vector with TSVAVEKR kex sequence.

This expression vector pAS25 (FIG. 6) contains the *T. reesei* cbhI promoter and terminator regions allowing for a strong inducible expression of a gene of interest and the *T. reesei* pyr2 selective marker conferring growth of transformants on minimal medium in the absence of uridine. The plasmids are maintained autonomously in fungal cells due to *T. reesei* derived telomere regions. The expression vector also contained CBH1 core exons 1 and 2 and partially 3, wherein there it is cut off and sequence of ccdB and chloramphenicol resistance marker is between this and the partial CBH1 terminator. In order to put cassettes of interest into this vector, the ccdB and chloramphenicol were cut out using restriction enzymes and gel purified for seamless assembly (geneart).

The HC fragment filled in the cbh1 core missing from the plasmid with homology at the 5' end, HC itself, CBH1 terminator, and a 48mer adapter arm for connecting with the LC cassette. The LC cassette utilized the 48mer adaptor for homology on the 5' end, CBH1 promoter, CBH1 core, LC, cbh1 terminator and homology to the vector at the 3' end. These cassettes were generated by PCR and DpnI treated before being purified. All 3 fragments were combined and seamless assembled (Geneart) and transformed into commercially available *Escherichia coli* TOP10 cells (Invitrogen, US). Four to six colonies per variant combination were picked, plasmid purified, and diagnostically cut with restriction enzyme NotI and analyzed on the ZAG fragment analyzer (Advanced Analytical) to assess which clones were correctly assembled. The correctly assembled vectors were then sent to sanger sequencing to ensure correct sequences. Plasmids were propagated in commercially available *Escherichia coli* TOP10 cells (Invitrogen, US), purified, arrayed individually in 96 well MTPs and used for fungal transformation as previously described supra.

As shown in Table 2, the combinatorials also resulted in increased to complete KEX2-mediated cleavage of the fusion polypeptide.

TABLE 2

Combinatorial variant cleavage sites
with improved cleavage efficiency

| Variant | CBH1 PI | position |
|---|---|---|
| S480H-Q487D | 15.9 | S2-Q6 |
| S480H-V483L | 37.6 | S2-V4 |
| S480H-V483L-E484W | 15.9 | S2-V4-E5 |
| S480K-A482R-Q487D-V488L | 16.0 | S2-V4-Q6-V7 |
| S480K-Q487D-V488L | 25.0 | S2-Q6-V7 |
| S480N-Q487D | 28.3 | S2-Q6 |
| T479E-S480H | 9.0 | T1-S2 |
| T479E-S480H-V483L-E484W | 8.2 | T1-S2-V4-E5 |
| T479E-S480P-V483L-E484W | 23.8 | T1-S2-V4-E5 |
| T479E-V483L-E484W | 18.6 | T1-V4-E5 |
| T479N-S480H-V483L-E484W | 26.0 | T1-S2-V4-E5 |
| V483L-E484W | 17.1 | V4-E5 |
| T479E-S480H-E484W | 22.4 | T1 - S2-E5 |
| T479E-S480H-V483L | 29.1 | T1 - S2-V4 |
| T479R-A482R-Q487D | 15.7 | T1 - A3-Q6 |
| T479R-A482R-Q487D-V488L | 26.5 | T1-A3-Q6-V7 |
| T479R-S480K-A482R-Q487D | 24.3 | T1 -S2-A3-Q6 |
| T479R-S480K-A482R-Q487D-V488L | 25.8 | T1 -S2-A3-Q6-V7 |
| T479R-S480K-A482R-V488L | 10.3 | T1 -S2-A3-V7 |
| T479R-S480K-Q487D-V488L | 12.5 | T1 -S2-Q6-V7 |

Additionally, SELs were created for an additional two amino acids in both the KEX2 pre- and post-cleavage site as shown below:

$$G_{-2}\text{-}P_{-1}\text{-}T_1\text{-}S_2\text{-}V\text{-}A_3\text{-}V_4\text{-}E_5\text{-}X_1\text{-}X_2\text{-}Q_6\text{-}V_7\text{-}T_8\text{-}L_9$$
(SEQ ID NO: 65)

Surprisingly, certain substitutions at these additional sites resulted in improved or complete cleavage when used in combination with the substitutions shown in Table 1. In particular, the $T_8$ position substituted with an alanine and the $L_9$ position substituted with an isoleucine resulted in complete cleavage when used in combination with one or more of the substitutions shown in Table 1 as well as the $G_{-2}$ position substituted with a tyrosine and the $P_{-1}$ position substituted with a threonine (Table 3). Additional highly combinable substitutions were found to be at $S_2$ (His) and $V_4$ (Leu) (Table 3).

TABLE 3

Combinatorial variant expanded cleavage
sites with improved cleavage efficiency

| Variant | CBH1 PI | position |
|---|---|---|
| G477Y-P478L-A482M-V483L | 26.3 | $G_{-2}$ - $P_{-1}$ - A3-V4 |
| G477Y-P478L-S480H-A482M-V483L | 35.2 | $G_{-2}$ - $P_{-1}$ - S2-A3-V4 |
| G477Y-P478T-S480H-A482M-V483L | 13.6 | $G_{-2}$ - $P_{-1}$ - S2-A3-V4 |
| G477Y-P478T-S480K-A482M-V483L | 15.2 | $G_{-2}$ - $P_{-1}$ - S2-A3-V4 |
| G477Y-S480H-A482M-V483L | 28.8 | $G_{-2}$ - S2-A3-V4 |
| G477Y-S480H-V483L | 17.8 | $G_{-2}$ - S2-V4 |
| P478L-A482M | 26.3 | $P_{-1}$ - A3 |
| P478L-S480H-A482M-V483L | 38.6 | $P_{-1}$ - S2-A3-V4 |
| Q487D-T489A | 9.1 | Q6-T8 |
| S480H-L490I | 25.8 | S2-L9 |
| S480H-Q487D-T489A | 58.2 | S2 - Q6- T8 |
| S480H-T489A | 22.6 | S2 - T8 |
| S480N-T489A | 20.5 | S2- T8 |
| S480N-V483L-Q487D-T489A | 29.4 | S2-V4-Q6-T8 |
| V483L-Q487D-T489A | 42.2 | V4-Q6 -T8 |

Example 4: Generation and Testing of Variants in an Additional Antibody

The improved linker variants identified in the previous examples were tested for cleavage efficiency in the generation of the monoclonal anti-HER2/neu antibody trastuzumab (Herceptin®).

Vector construction: The expression vectors contained the *T. reesei* cbhI promoter and terminator regions which provided for strong inducible expression of a gene of interest, CBH1 core, light chain or heavy chain connected by CBH1 linker and kex2 for processing of CBH1. The light chain vectors contain the *Aspergillus nidulans* amdS selective marker conferring growth on minimal media with acetamide as the sole nitrogen source. The heavy chain vectors contain the *T. reesei* pyr2 selective marker conferring growth on minimal media in the absence of uridine. The vector construction was completed and delivered by Twist Biosciences (San Francisco, CA). Overall, 4 vectors were constructed: 2 containing light chain and 2 containing the heavy chain of the antibody trastuzumab. For each chain, the linker portion either contained or did not contain an S480K mutation so that the effectiveness of processing the antibody chain from the fusion partner CBH1 was able to be evaluated.

Fungal strain and transformation: To assess the effectiveness of the linker mutation S480K, transformations of all combinations with or without the S480K mutation on both heavy and light chain were tested. Since the light and heavy chains are on separate vectors with different selectable markers, the heavy and light chain vectors were co-transformed together into the host *T. reesei* strain. The plasmids were maintained autonomously in fungal cells due to *T. reesei* derived telomere regions. Usage of replicative plasmids resulted in increased frequencies of transformation and circumvented problems of locus-dependent expression observed with integrative fungal transformation.

The host *T. reesei* strain used for transformation was deleted for major cellulases and xylanases. The strain was transformed using a standard PEG-protoplast transformation method. Transformation mixtures containing approximately 1 μg of each vector DNA and $5\times10^6$ protoplasts in a total volume of 250 μL were treated with 2 mL of 25% PEG solution, diluted with 2 volumes of 1.2M sorbitol/10 mM Tris, pH7.5/10 mM CaCl$_2$ solution, and mixed with 8 mL of 2% low melting agarose containing 1M sorbitol, 20 mM acetamide in minimal medium and distributed over a 10 cm petri plates pre-poured containing 1.5% agarose, 1M sorbitol, 20 mM acetamide in minimal media. After sufficient growth, transformants were pooled together and plated on fresh petri agar plate with minimal medium containing 10 mM acetamide as a sole nitrogen source. Once sporulated, spores were harvested and used for inoculation of liquid cultures.

To generate sufficiently high antibody titers, $10^5$-$10^6$ T. reesei spores were inoculated in customer-made 24 well MTPs composed of the Sylgard 170 elastomer (from Dow Corning, USA) premixed with lactose which was slowly released in the medium during fermentation to ensure continuous production. Cultures were grown in 1 ml of medium containing: 16 g/L glucose, 9 g/L casamino acids, 10 g/L (NH4)2SO4, 4.5 g/L KH2PO4, 1 g/L MgSO4*7H2O, 1 g/L CaCl2*2H2O, 33 g/L PIPPS buffer [pH 5.5], 0.25% T. reesei trace elements.

Plates were incubated in an Infors shaker with a 50 mm throw at 200 rpm and 28 C with 80% humidity. After 5-6 days of growth cultures were reformatted back to 96 well deep well MTPs and filtered using 96-well microtiter filter plates (0.2 μm hydrophilic PVDF membrane, Corning, Tewksbury MA). Clarified samples were analyzed for the expression of antibody by western blot using premixed heavy and light chain specific antibody peroxidase conjugate from Promega (Madison, WI).

Figure 9:
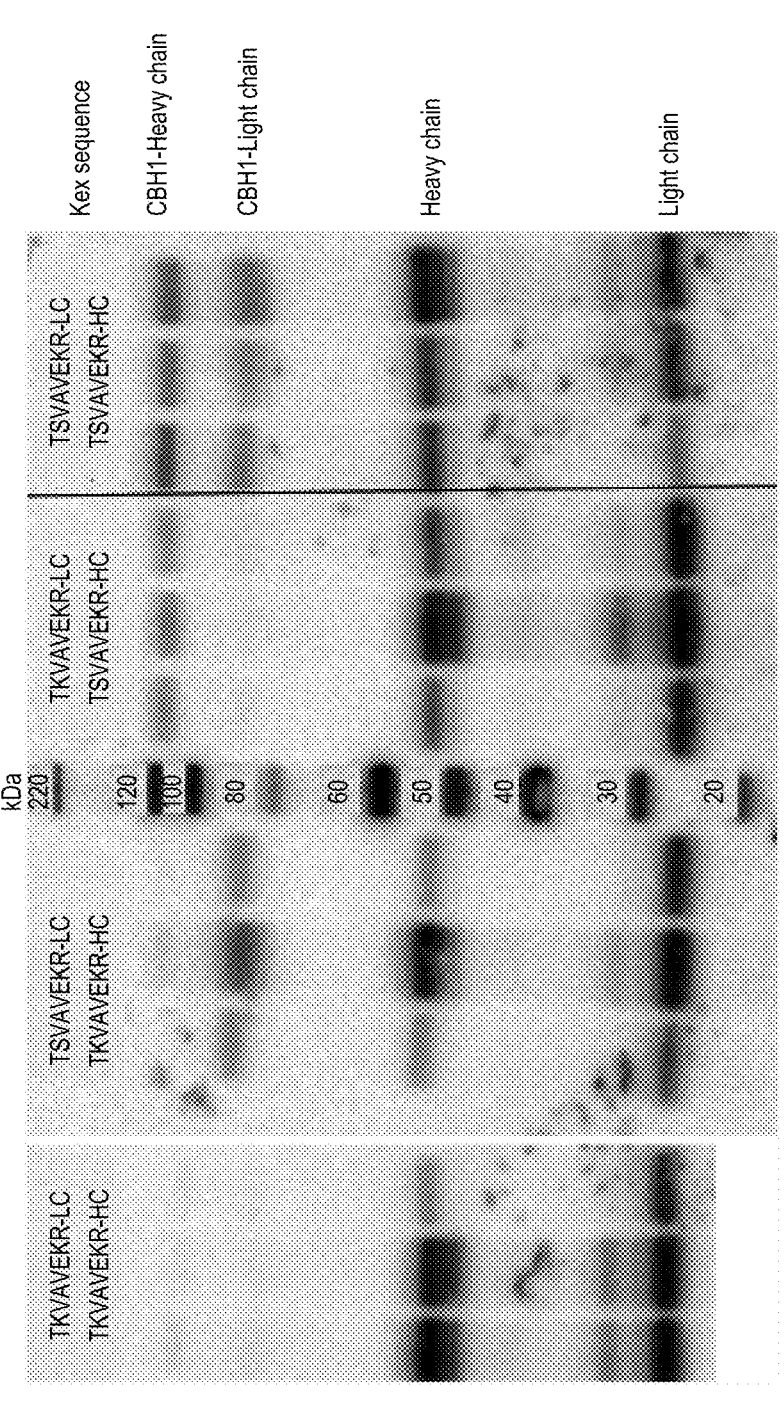
FIG. 9 depicts the results of a western blot showing cleavage of trastuzumab from CBH1.

Results: Trastuzumab light and heavy chain expressed with or without the S480K mutation was evaluated for full CBH1 processing by western blot. Shown in FIG. 9, when the S480K mutation is present in either heavy or light chain, it is almost fully processed from CBH1. Conversely, if the mutation is not present, there is noticeable signal of CBH1 not fully processed from the heavy or light chain. This mutation is therefore essential for improved to complete processing of CBH1 from the trastuzumab antibody chains.

We claim:

1. A fusion polypeptide comprising a KEX2 region, wherein the amino acid sequence of the KEX region comprises TKVAVEKRQV (SEQ ID NO:10), wherein the amino acid sequence is completely cleaved by one or more protease(s) and wherein the protease is a Kex2 serine peptidase (EC 3.4.21.61).

2. The fusion polypeptide of claim 1, further comprising a polypeptide encoding a signal sequence.

3. The fusion polypeptide of claim 2, wherein the polypeptide encoding a signal sequence is located N-terminal or C-terminal from the amino acid sequence of the KEX region.

4. The fusion polypeptide of claim 1, further comprising a polypeptide encoding a carrier protein.

5. The fusion polypeptide of claim 4, wherein the polypeptide encoding a carrier protein is located N-terminal or C-terminal from the amino acid sequence of the KEX region.

6. The fusion polypeptide of claim 5, wherein the polypeptide encoding a carrier protein is adjacent to the polypeptide encoding a signal sequence.

7. The fusion polypeptide of claim 5, wherein the carrier protein comprises CBH1 or a fragment thereof.

* * * * *